(12) United States Patent
Servant et al.

(10) Patent No.: US 10,215,759 B2
(45) Date of Patent: *Feb. 26, 2019

(54) ELECTROPHYSIOLOGICAL ASSAYS USING OOCYTES THAT EXPRESS HUMAN ENAC AND THE USE OF PHENAMIL TO IMPROVE THE EFFECT OF ENAC ENHANCERS IN ASSAYS USING MEMBRANE POTENTIAL REPORTING DYES

(71) Applicant: SENOMYX, INC., San Diego, CA (US)

(72) Inventors: Guy Servant, San Diego, CA (US); Hong Chang, San Diego, CA (US); Cyril Redcrow, San Diego, CA (US); Sumita Ray, San Diego, CA (US); Imran Clark, Carlsbad, CA (US); Bryan Moyer, San Diego, CA (US)

(73) Assignee: SENOMYX, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/257,517

(22) Filed: Sep. 6, 2016

(65) Prior Publication Data
US 2017/0175160 A1 Jun. 22, 2017

Related U.S. Application Data

(60) Division of application No. 10/563,758, filed as application No. PCT/US2004/021853 on Jul. 9, 2004, now Pat. No. 9,459,259, and a continuation-in-part of application No. 10/133,573, filed on Apr. 29, 2002.

(60) Provisional application No. 60/485,745, filed on Jul. 10, 2003, provisional application No. 60/287,413, filed on May 1, 2001.

(51) Int. Cl.
| | |
|---|---|
| C12Q 1/02 | (2006.01) |
| C12N 15/85 | (2006.01) |
| G01N 33/50 | (2006.01) |
| G01N 33/68 | (2006.01) |

(52) U.S. Cl.
CPC ......... *G01N 33/6872* (2013.01); *C12N 15/85* (2013.01); *C12Q 1/025* (2013.01); *G01N 33/5044* (2013.01); *C12N 2320/10* (2013.01); *C12N 2503/02* (2013.01); *G01N 2500/10* (2013.01)

(58) Field of Classification Search
None
See application file for complete search history.

(56) References Cited

U.S. PATENT DOCUMENTS

| | | |
|---|---|---|
| 5,693,756 A | 12/1997 | Xiao-Jiang et al. |
| 5,892,018 A * | 4/1999 | Welsh .................. C07K 14/705 435/320.1 |
| 6,083,986 A | 7/2000 | Castle et al. |
| 6,287,859 B1 | 9/2001 | DeWeille et al. |
| 6,524,798 B1 | 2/2003 | Goldbard et al. |
| 2002/0128203 A1 | 9/2002 | Schild et al. |
| 2002/0168625 A1 | 11/2002 | Weaver et al. |
| 2004/0072254 A1 | 4/2004 | Callamaras et al. |
| 2005/0037369 A1 | 2/2005 | Neote et al. |
| 2005/0059094 A1 | 3/2005 | Servant et al. |
| 2005/0177886 A1 | 8/2005 | Margolskee et al. |
| 2006/0089306 A1 | 4/2006 | Wallace et al. |
| 2006/0223117 A1 | 10/2006 | Moyer et al. |
| 2007/0071757 A1 | 3/2007 | Yu et al. |
| 2009/0253159 A1 | 10/2009 | Maher et al. |

FOREIGN PATENT DOCUMENTS

| | | |
|---|---|---|
| WO | 2002/087306 | 7/2002 |
| WO | 2005/015158 | 2/2005 |
| WO | 2007/146120 | 12/2007 |

OTHER PUBLICATIONS

Mick et al., Molecular Endocrinology, Apr. 1, 2001; 15: 575-588. (Year: 2001).*
González et al., DDT, 1999; 4: 431-439. (Year: 1999).*
Li et al., Molecular Pharmacology, 1995; 47: 1133-1140. (Year: 1995).*
Waldmann R, et al. "Molecular cloning and functional expression of a novel amiloride-sensitive Na+ channel," J Biol Chem. Nov. 17, 1995;270(46):27411-4.
Denyer, et al. "HTS approaches to voltage-gated ion channel drug discovery," DDT, vol. 3, No. 7, Jul. 1998: 323-332.

(Continued)

*Primary Examiner* — Christina M Borgeest
(74) *Attorney, Agent, or Firm* — Robin L. Teskin; LeClairRyan PLLC

(57) ABSTRACT

In one aspect, the present invention relates to a mammalian cell-based high-throughput assay for the profiling and screening of human epithelial sodium channel (hENaC) cloned from a human kidney c-DNA library and is also expressed in other tissues including human taste tissue. The present invention further relates to amphibian oocyte-based medium-throughput electrophysiological assays for identifying human ENaC modulators, preferably ENaC enhancers. Compounds that modulate ENaC function in a cell-based ENaC assay are expected to affect salty taste in humans. The assays described herein have advantages over existing cellular expression systems. In the case of mammalian cells, such assays can be run in standard 96 or 384 well culture plates in high-throughput mode with enhanced assay results being achieved by the use of a compound that inhibits ENaC function, preferably an amiloride derivative such as Phenamil. In the case of the inventive oocyte electrophysiological assays (two-electrode voltage-clamp technique), these assays facilitate the identification of compounds which specifically modulate human ENaC. The assays of the invention provide a robust screen useful to detect compounds that facilitate (enhance) or inhibit hENaC function. Compounds that enhance or block human ENaC channel activity should thereby modulate salty taste in humans.

12 Claims, 11 Drawing Sheets

Specification includes a Sequence Listing.

(56) References Cited

OTHER PUBLICATIONS

Qi J, et al. "Regulation of the amiloride-sensitive epithelial sodium channel by syntaxin 1A," J Biol Chem. Oct. 22, 1999;274(43):30345-8.

Birch PJ, et al. "Strategies to identify ion channel modulators: current and novel approaches to target neuropathic pain," Drug Discov Today. May 1, 2004;9(9):410-8.

Ishikawa T, et al. "Electrophysiological characterization of the rat epithelial Na+ channel (rENaC) expressed in MDCK cells. Effects of Na+ and Ca2+," J Gen Physiol. Jun. 1998;111(6):825-46.

Li XJ, et al. "Alternatively spliced forms of the alpha subunit of the epithelial sodium channel: distinct sites for amiloride binding and channel pore," Mol Pharmacol. Jun. 1995;47(6):1133-40. [Abstract Only, 4 pages].

McDonald FJ, et al. "Cloning and expression of the beta- and gamma-subunits of the human epithelial sodium channel," Am J Physiol. May 1995;268(5 Pt 1):C1157-63.

Li et al, Expression and localization of amiloride-senstitve sodium channel indicate a role for non-taste cells in taste perception, Proc Natl Acad Sci, 91(5), 1814-1818, 1994.

Barbry P, et al. "Purification and subunit structure of the [3H]phenamil receptor associated with the renal apical Na+ channel," Proc Natl Acad Sci U S A. Jul. 1987;84(14):4836-40.

\* cited by examiner

Z' (range)   # of experiments
>0.5   153
0.2 to 0.5   417
0 to 0.2   149
<0   116

FIGURE 8  % Enhancement Factor = [(A-Ao)/(B-Bo)] x -100%
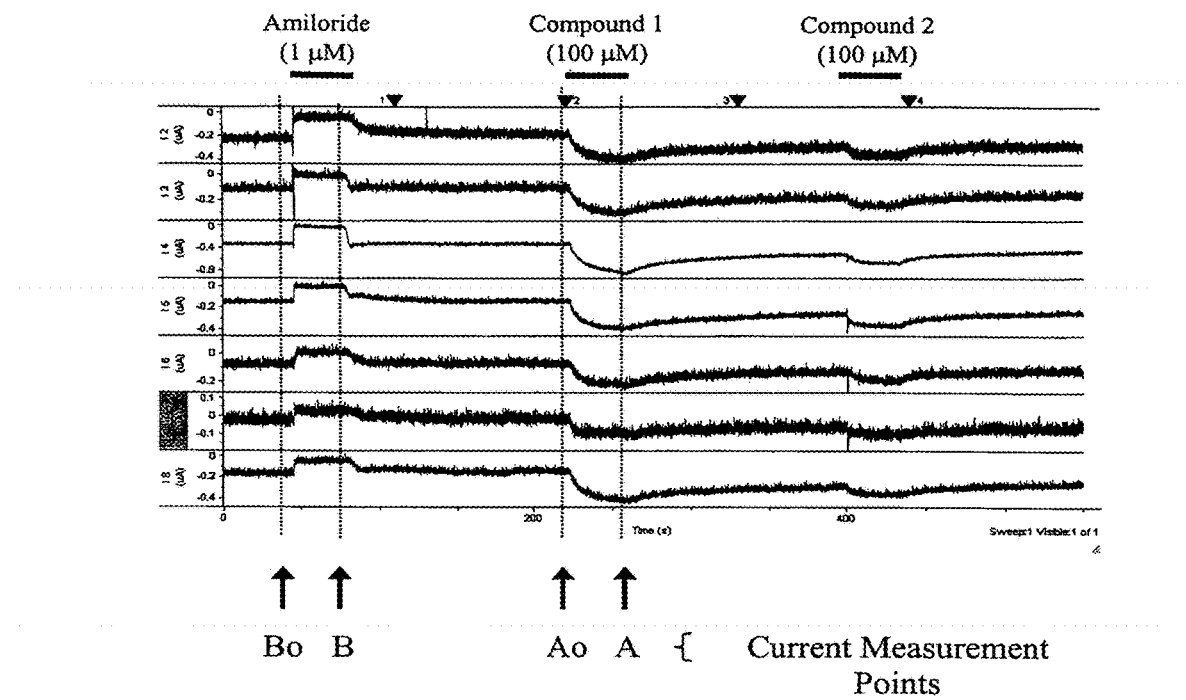
FIGURE 9  Quantitation of ENaC Enhancement
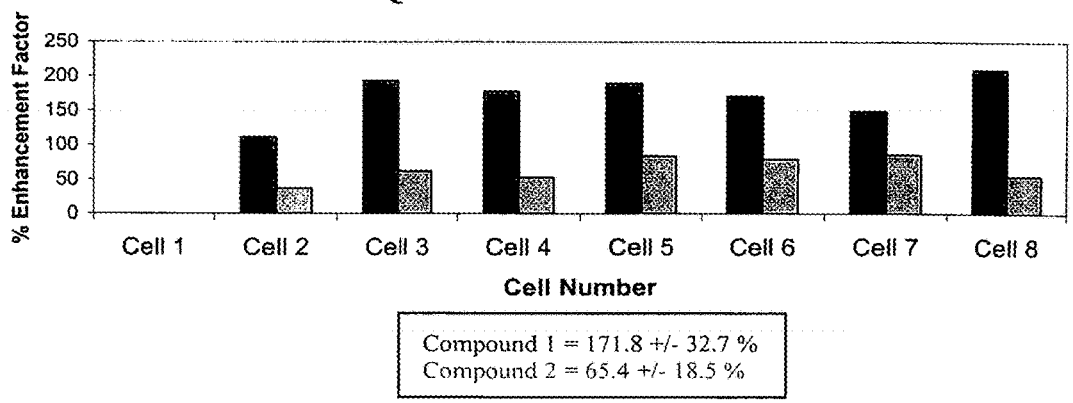

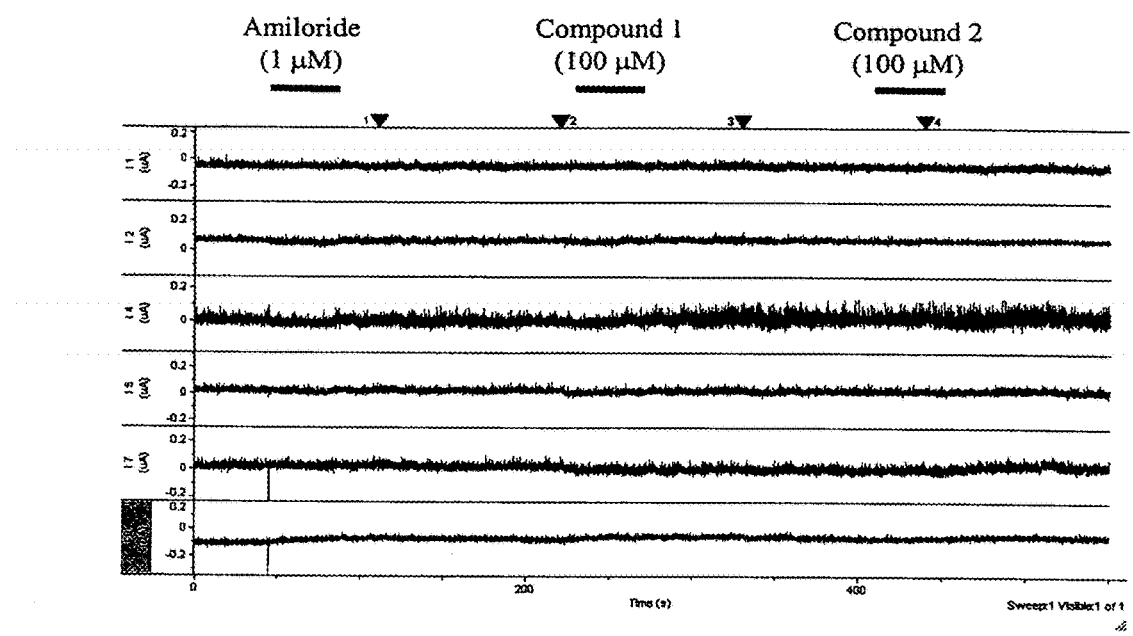
FIGURE 10  Example Uninjected Oocytes

Example I/V Curves
Figure 11A Injected eggs
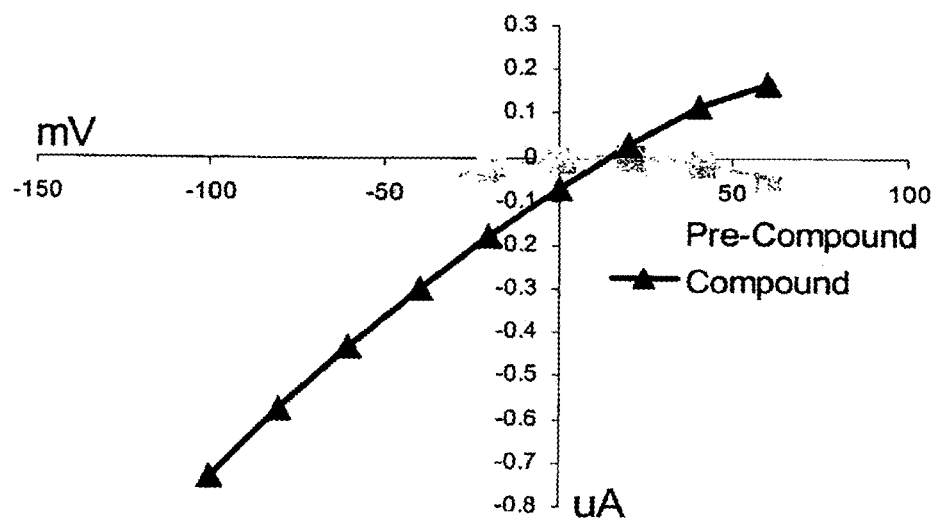
Figure 11B Uninjected eggs
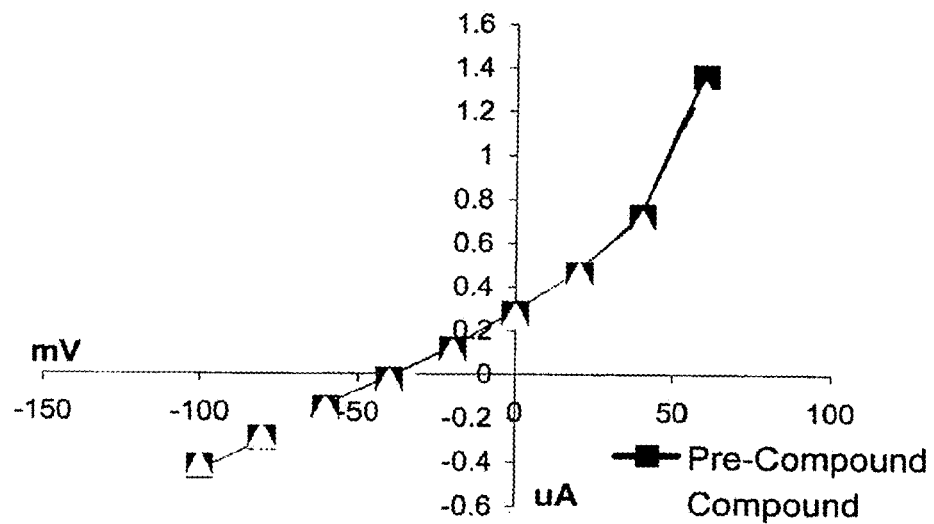

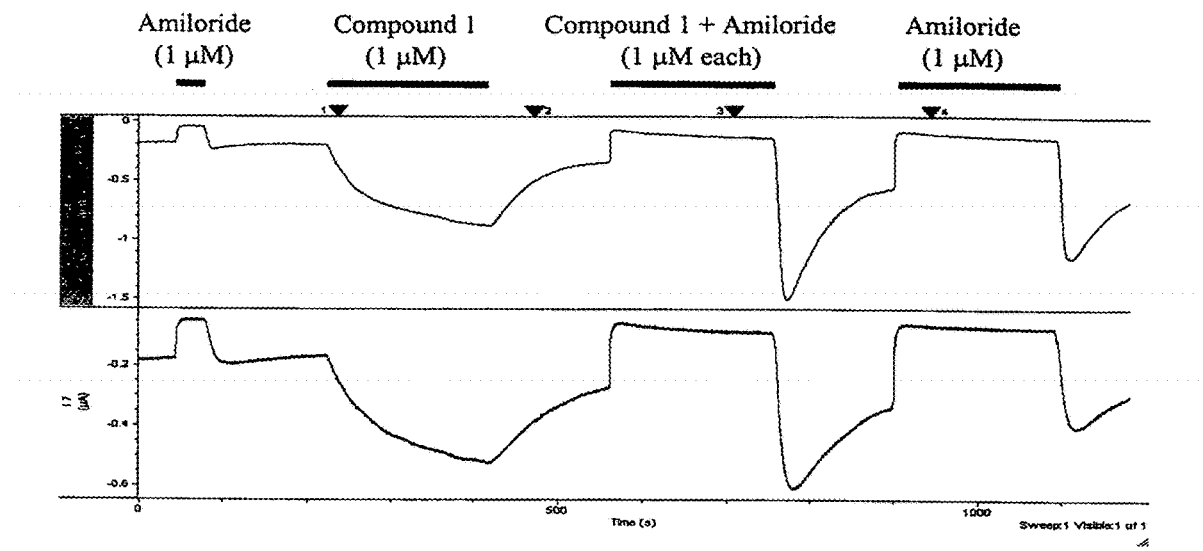
FIGURE 13    Example Dose Response Curves
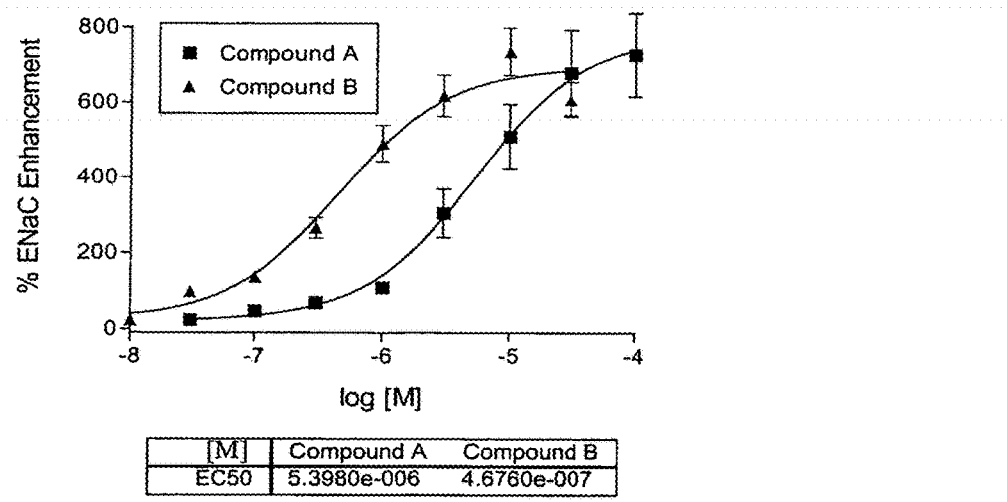

FIGURE 14  ENaC Oocyte Assay Flowchart
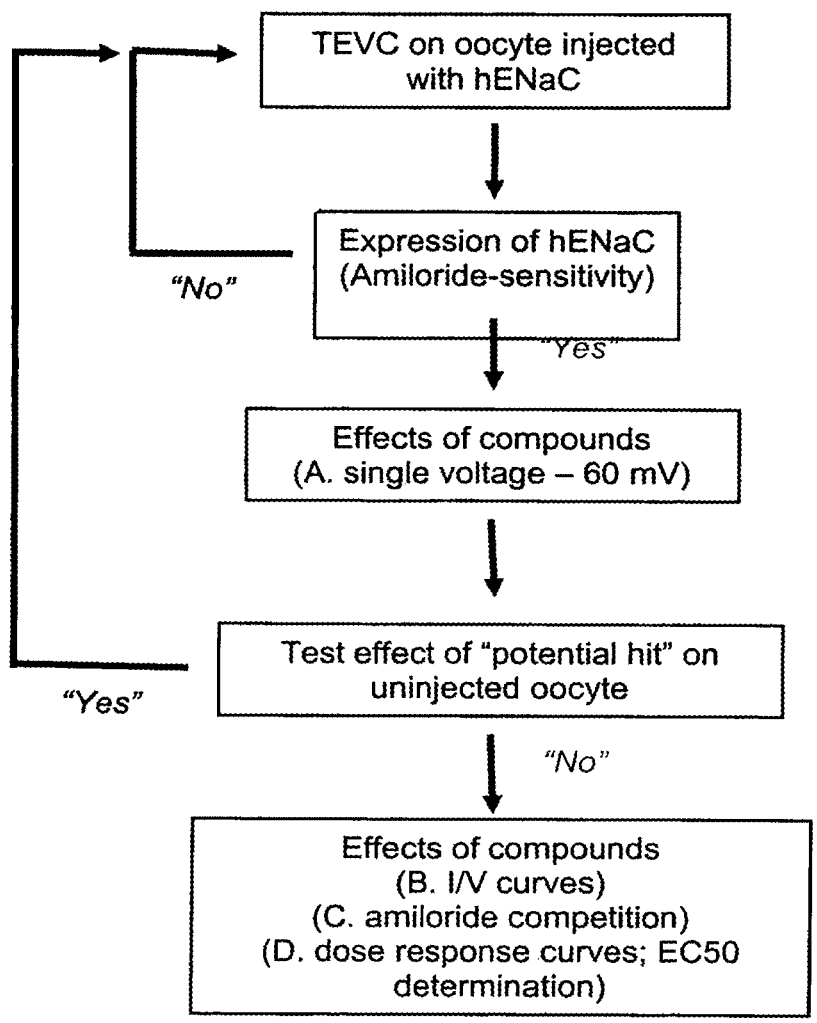

ELECTROPHYSIOLOGICAL ASSAYS USING OOCYTES THAT EXPRESS HUMAN ENAC AND THE USE OF PHENAMIL TO IMPROVE THE EFFECT OF ENAC ENHANCERS IN ASSAYS USING MEMBRANE POTENTIAL REPORTING DYES

CROSS REFERENCE TO RELATED APPLICATIONS

This application is a divisional of U.S. Ser. No. 10/563,758 filed on Mar. 6, 2008, which is a 371 of PCT/US04/21853 filed Jul. 9, 2004 which claims benefit of U.S. Provisional No. 60/485,745 filed on Jul. 10, 2003 and said U.S. Ser. No. 10/563,758 is a CIP of U.S. application Ser. No. 10/133,573 filed on Apr. 29, 2002 which claims priority to U.S. Provisional Application No. 60/287,413 filed on May 1, 2001, all of which are incorporated herein by reference in their entireties.

The present invention involves the discovery that the efficacy of cell-based assays that screen for compounds that modulate ENaC function, preferably ENaC enhancers, is improved by the further use of a compound that at least partially inhibits ENaC function preferably an amiloride derivative such as phenamil. The present invention further relates to improved electrophysiological assays that identify human ENaC modulators using oocytes, preferably frog oocytes, that express a functional human ENaC sodium channel.

FIELD OF THE INVENTION

The present invention in part relates to novel cell based assays that use recombinant host cells that express amiloride-sensitive sodium channels to profile, screen for, and identify taste modulating compounds. More specifically, the invention relates to assays that utilize test cells that express a functional human epithelial sodium channel (hENaC), preferably amphibian oocytes or mammalian cells, and the use of these test cells in cells in high throughout or moderate throughput cell-based assays, preferably electrophysiological assays, to identify compounds that enhance or block hENaC function.

BACKGROUND OF THE INVENTION

An amiloride-sensitive epithelial sodium channel (ENaC) mediates sodium influx across the apical membrane of taste buds cells in the tongue (Heck, et al, Science (1984) 223: 403-405). ENaC, a member of the ENaC/degenerin superfamily of ion channels involved in sodium transport, is composed of three partially homologous α, β, and γ subunits expressed at both the RNA and protein level in fungiform, follate, and circumvallate papilla as well as the lingual epithelium in taste tissue (Li, et al, Proc. Natl. Acad. Sci. (1994) 91: 1814-1818; Kretz, et al, J. Histochem. Cytochem. (1999) 47(1): 51-64; Lin, et al, J. Comp. Neurol. (1999) 405: 406-420; Xiao-Jiang, et al, Mol. Pharmacol. (1995) 47: 1133-1140).

Complementary DNAs (cDNAs) encoding amiloride-sensitive epithelial sodium channel (ENaC) channel subunits have been isolated from kidney cells and expressed in a mammalian cell line. The channel expressed in this system has been shown to have similar properties to the distal renal sodium channel, i.e., high sodium selectivity, low conductance, and amiloride sensitivity. One form of the naturally occurring ENaC channel is comprised of three subunits of similar structure: alpha (OMIM Entry 600228), beta (OMIM Entry 600760), and gamma (OMIM Entry 600761). Each of the subunits is predicted to contain 2 transmembrane spanning domains, intracellular amino-and carboxy-termini, and a cysteine-rich extracellular domain. The three subunits share 32 to 37% identity in amino acid, sequence. Alternatively spliced forms of alpha-ENaC have also been identified, indicating heterogeneity of alpha subunits of amiloride-sensitive sodium channels that may account for the multiple species of proteins observed during purification of the channel (See U.S. Pat. No. 5,693,756, which is herein incorporated by reference).

An inhibitor of ENaC sodium channel function, amiloride, is known to attenuate gustatory responses to sodium chloride in numerous non-mammalian as well as mammalian species, including humans (Halpern, Neuroscience and Behavior Reviews (1998) 23: 5-47 and all references cited within; Liu, et al, Neuron (2003) 39: 133-146; Zhao, et al, Cell (2003) 115: 255-266). In humans, amiloride reportedly reduces the intensity of sodium chloride by 15-20% when used at concentrations that specifically inhibit ENaC function (Halpern, Neurosciences and Behavior Reviews (1998) 23:5-47 and all references cited within; Feldman, et al, J. Neurophysiol. (2003) 90(3): 2060-2064). Therefore, compounds that increase the transport of sodium ions through ENaC channels may function as general salt taste enhancers and augment human salt taste perception as suggested in our previous patent application (PCT WO 02/087306 A2). Further, based on published electrophysiological data and the discovery that a human ENaC is expressed in taste bud cells, a model of salty taste transduction mediated by ENaC has been constructed. As such, the use of ENaC in the identification of substances which stimulate or block salty taste perception has been suggested (See U.S. Pat. No. 5,693,756, supra and PCT WO 02/087306 A2).

Cell-based functional expression systems commonly used for the physiological characterization of. ENaC are *Xenopus laevis* oocytes and cultured mammalian cell lines. The oocyte system has advantages over mammalian cells in that it allows the direct injection of multiple mRNAs, provides high levels of protein expression, and can accommodate the deleterious effects inherent in the over expression of ENaC. However, the drawbacks of this system are that electrophysiological recording in *Xenopus* oocytes is not amenable to screening large numbers of compounds and the *Xenopus* oocyte is an amphibian not a mammalian system. Studies of the electrophysiological properties of rodent ENaC in mammalian cell lines (HEK293 and M DCK) stably expressing the channel have been reported in the literature. While these studies used mammalian cell lines, channel function was assayed using tedious electrophysiological techniques. Such approaches do not lend themselves to high throughput screening of compounds. Thus, there remains a need in the art for identification of salt taste enhancers amenable to high throughput screening.

The development of salt taste enhancers has been the focus of numerous prior scientific publications and patents. However, direct modulation of the ENaC sodium channel involved in salt taste perception is a novel and unique approach to enhance human salty taste. Some examples of previously reported salt enhancing compounds and their properties are discussed below.

Some proteolzyed proteins, peptides, amino acids, and amino-acid esters reportedly function as salt enhancers (Tamura, et al, Argic. Biol. Chem. (1989) 53(6): 1625-1633, 1989; U.S. Pat. No. 5,711,985). However, these agents require high concentrations, between 30-60 mM, and must be supplemented with hydrochloride acid to positively modulate salty taste. In addition, the cost and difficulty in synthesizing these compounds are prohibitive for their large-scale commercial use as salt enhancers for the general population.

Choline chloride, an ammonium salt classified by the federal government a s a GRAS (generally regarded as safe) compound, has been reported to function as a salt enhancer in humans and rodents. In humans, choline chloride increases the saltiness of dilute salt solutions (less than 50 mM NaCl) by a factor of two and reportedly increases the preference or hedonic ratio of both cooked peas and Campbell's low salt tomato soup (Locke, et al, Physiology & Behavior (1994) 55(6): 1039-1046; U.S. Pat. Nos. 5,260,091; 5,260,049). However, similar to peptides and amino acids described above, choline chloride requires significant concentrations (in the mM range) to enhance salty taste.

Derivatives of amiloride, which do not block ENaC function but instead block sodium-proton exchange, as well as chloride channel blockers, such as IAA-94 and anthranilic acid, reportedly increase fluid intake; an indirect measurement of salt consumption, in a rodent model system (U.S. Pat. No. 5,260,091). However, the utility of these agents as human salt enhancers has not been reported.

Cetylpyridiunium chloride (CPC) has been reported to increase amiloride-insensitive nerve responses to salt in rats and to enhance the saltiness of low salt Campbell's tomato soup by 50% in humans when used at low concentrations (high uM range) (DeSimone, et al, J. Neurphysiol. (2001) 86: 2638-2641; U.S. Pat. No. 4,997,672). However, CPC is a detergent and based on its structure likely intercalates into lipid bilayers of cells and thereby non-specifically activates salt taste cells by disrupting lipid homeostasis.

Indeed, high concentrations of CPC (low mM range), above the critical micelle concentration, actually inhibit rat nerve responses to numerous salty compounds including sodium chloride, potassium chloride, and ammonium chloride, further substantiating that the reportedly observed CPC effects were likely non-specific.

Trehalose, a disaccharide composed of two glucose molecules, reportedly increases the saltiness of sodium chloride solutions by 1.2 to 2-fold (U.S. Pat. No. 6,159,529). Similar to peptides and choline chloride, high levels (1.5-12%) of this sugar are required to enhance saltiness, suggesting that the observed effects could be non-specific and attributable to taste cell volume changes (cell shrinkage) due to hyperosmolarity. In addition, the specificity of trehalose and other aforementioned salt enhancers to enhance salty taste and not modulate other tastes, including sweet, bitter, sour, and umami, was not addressed.

Alapyridaine, a derivative of the amino acid alanine that is formed as a by-product in heated sugar/amino acid mixtures, reportedly decreases the threshold for detecting sodium chloride 5-fold (Soldo, et al, Chemical Senses (2003) 28: 371-379, 2003; Ottinger, et al, J. Agric Food Chem (2003) 51: 1035-1041, 2003). Alapyridaine, however, reportedly functions as a general taste enhancer and decreases the detection thresholds for salt as well as sweet and umami tastes. In addition, the effect of alapyridaine on salt taste at higher, more physiologically-relevant, salt concentrations was not disclosed. Thus, the effects of alapyridaine may only surface when tasting low salt concentrations near threshold detection-levels.

The antibiotic novobiocin also reportedly enhances nerve responses to sodium chloride in rats (Feigin, et al, Am. J. Physiol. (1994) 266: C1165-C1172). However, disadvantageously novobiocin reportedly forms amiloride-insensitive cation-selective ion channels in lipid bilayers suggesting that this agent pokes holes in cell membranes and, perhaps similar to CPC, non-specifically increase taste cell activity. The effect of novobiocin on human salt taste perception has not been reported.

Bretylium tosylate, an anti-fibrillary drug that modulates adrenergic and muscarinic receptors, has been reported to specifically potentiate salt taste in rodents and humans without affecting sweet, sour, or bitter taste (Schiffman, et al, Physiology & Behavior (1986) 36: 1129-1137). However, a significant disadvantage of bretylium tosylate, separate from the relatively high concentrations required to positively modulate salty taste (mM range), is that the compound is a therapeutic used to treat cardiac patients. Consequently this compound would be unsuitable for use in the general population.

Glybenclamide, an inhibitor of members of the ATP-binding cassette (ABC) protein superfamily, including the cystic fibrosis transmembrane conductance regulator and the sulfonylurea receptor, reportedly increases amiloride-sensitive ENaC sodium current by doubling the open probability of individual ENaC channels (Chraibi, et al, The Journal of Pharmacology and Experimental Therapeutics (1999) 290: 341-347, 1999; Schnizler, et al, Biochemica et Biophysica Acta (2003) 1609: 170-176). However, because Glybenclamide modulates ABC protein function, it is probable that Glybenclamide effects are due to indirect modulation of ENaC activity by ABC proteins and not attributable to direct modulation of ENaC channel function. In addition, glybenclamide has not been demonstrated to enhance human salt taste perception nor has glybenclamide been suggested as a salt taste enhancer.

Thus, based on the foregoing, it is evident that improved methods for identifying compounds that specifically modulate ENaC and salty taste are needed as are improved salty taste modulators. Preferably, such methods will comprise high or medium throughput methods and will screen for compounds having a direct effect on human ENaC function.

SUMMARY OF THE INVENTION

The present invention obviates the problems of the prior art, relating to assays for identifying compounds that modulate ENaC. Specifically, the present invention provides cell-based assays that utilize recombinant host cells, preferably mammalian cells or oocytes that express a functional human ENaC to identify compounds that modulate ENaC and consequently salty taste. More specifically, the present invention provides oocyte and mammalian cell-based assays, preferably high or medium throughput, for the profiling and screening of a sodium channel, more particularly an amiloride-sensitive epithelial sodium channel (ENaC), which assays optionally may include the addition of a compound that partially or totally inhibits ENaC function, preferably amiloride or an amiloride derivative such as phenamil. It has been found that the use of phenamil in particular enhances signal intensity during assays, preferably high or medium throughput assays for identifying compounds that modulate (enhance or inhibit) ENaC function. Such methods can be used to functionally characterize ENaC activity or to identify compounds that either enhance or block salty taste perception (herein referred to as salty taste modulators).

Accordingly, in a first aspect the invention provides recombinant host cells, preferably mammalian cells or amphibian oocytes that express a functional hENaC. In a preferred embodiment these cells will transiently or stably express all three subunits of hENaC (alpha or delta, beta and gamma), or transiently or stably express one or more subunits or functional chimeras, variants or fragments thereof. Mammalian cells suitable for use in the invention encompass any mammalian cell capable of expressing a functional hENaC, including by way of example COS, CHO, MDCK, HEK293, HEK293T, NIH3T3, Swiss3T3 and BHK cells. However, in the preferred embodiment the invention provides HEK293T cells that express a functional hENaC. Oocytes useful in the invention preferably include amphibian oocytes, e.g., *Xenopus* oocytes.

In a second aspect, the invention provides cell-based assays that utilize mammalian cells or amphibian oocytes that express a functional ENaC, preferably hENaC, to identify compounds, including e.g., small organic molecules, antibodies, peptides, cyclic peptides, lipids and nucleic acids that enhance or block ENaC function. Preferably, these assays will include the addition of known ENaC inhibitor at a concentration that partially inhibits ENaC function prior to addition of use of one or more putative ENaC modulatory compounds.

Preferably the assay will comprise a mammalian or oocyte cell-based assay, preferably high or medium throughput, for the profiling and screening of putative modulators of an epithelial sodium channel (ENaC) comprising: (i) contacting a test cell expressing an ENaC loaded with a membrane potential fluorescent dye or a sodium-sensitive fluorescent dye with at least one putative modulator compound in the presence o f a buffer containing sodium; (ii) prior to the addition of said at least one putative modulator compound, contacting said host cell with a compound that is known to inhibit ENaC function, at a concentration whereby ENaC function is at least partially inhibited, preferably an amiloride derivative such as phenamil; and (iii) monitoring changes in fluorescence of the membrane potential dye or sodium-sensitive dye in cells contacted with the putative modulator plus sodium after addition of the known ENaC inhibitor compound compared to the change in fluorescence of the membrane potential dye or sodium-sensitive dye for cells contacted with sodium alone to determine the extent of ENaC modulation.

In another preferred aspect of the invention, a method for monitoring the activity of an epithelial sodium channel (ENaC) is provided comprising: (i) providing test cells, e.g., mammalian cells transfected or transformed with a functional ENaC; (ii) seeding the test cell in the well of a multi-well plate and incubating for a time sufficient to reach at least about 70% confluence; (iii) dye-loading the seeded test cells with a membrane potential fluorescent dye or sodium-sensitive fluorescent dye in the well of the multi-well plate; (iv) contacting the dye-loaded test cell with at least one putative modulatory compound in the well of the multi-well plate; (v) prior to the addition of said at least one putative modulatory compound, further contacting said host cell with a compound that partially inhibits ENaC function, e.g., an amiloride derivative such as phenamil; and (vi) monitoring any changes in fluorescence using a fluorescence plate reader.

In another preferred embodiment of the invention (i) suitable cells, e.g., HEK293T cells or another mammalian cell line are transformed, transfected with DNA sequences encoding subunits necessary to produce a functional human ENaC; (ii) the cells are seeded onto a multi-well plates, e.g., 384 well plates, preferably to about 80% confluence; (iii) the seeded test cells are loaded with a membrane potential sensitive dye such as CC2-DMPVE or DiSBAC2(3); (iv) the dye-loaded cells are then contacted with at least one putative ENaC modulatory compound; (v) the dye-loaded cells are preferably further contacted prior to contacting with said at least one ENaC modulatory compound with an amount of at least one known ENaC inhibitor at a concentration that results in at least partial ENaC inhibition; and (iv) monitoring changes in cell fluorescence using a voltage intensity plate reader e.g., VIPRII (Aurora Biosciences).

In yet another aspect of the invention, a method for identifying a salty taste modulatory compound is provided comprising: (i) providing test cells transfected, transformed with a functional human ENaC; (ii) seeding the test cell in the well of a multi-well plate and incubating for a time sufficient to reach at least about 70% confluence more preferably to about 80%, confluence; (iii) dye-loading the seeded test cells with a membrane potential dye in the well of the multi-well plate; (iv) contacting the dye-loaded test cells with at least one putative modulatory compound in the well of the multi-well plate; (v) preferably prior to the addition of said at least one putative modulatory compound further contacting the dye-loaded test cell with a known ENaC inhibitor compound at a concentration that at least partially inhibit ENaC function, e.g., an amiloride derivative such as phenamil; (vi) monitoring any changes in fluorescence of the membrane potential dye due to modulator/ENaC interactions using a fluorescence plate reader; and (vii) identifying the at least one putative modulator as a salty taste modulating compound based on the monitored changes in fluorescence.

In yet another preferred embodiment of the invention (i) suitable cells, e.g., HEK293T cells are transformed or transfected with DNA sequences encoding subunits necessary to produce a functional human ENaC; (ii) the cells are seeded onto multi-well plates, e.g., 384 well plates, preferably to about 80% confluence; (iii) the seeded test cells are loaded with a membrane potential sensitive dye such as CC2-DMPVE or DiSBAC2(3); (iv) the dye-loaded cells are then contacted with at least one putative ENaC modulatory compound; (v) preferably prior thereto the dye-loaded cells are contacted with a compound known to inhibit ENaC function, e.g., an amiloride derivative such as phenamil at a concentration that at least partially inhibits ENaC function; (vi) changes in cell fluorescence are monitored using a voltage intensity plate reader e.g., VIPRII (Aurora Biosciences); and (vii) compounds that modulate salty taste are selected based on a change in fluorescence intensity.

In yet another preferred embodiment of the invention, electrophysiological assays, preferably two-electrode voltage clamp assays are provided wherein human ENaC modulatory compounds are identified based on their effect (inhibitory or enhancing) on macroscopic electrical current in oocytes, preferably amphibian oocytes (frog)), that express a functional human EnaC sodium channel. These assays are an improvement over some other cell-based assays for identifying ENaC modulators, in part because oocytes express few endogenous ion channels; consequently the oocyte expression system advantageously allows direct measurement of ENaC sodium channel current with little or no background.

In another preferred embodiment of the invention, these electrophysiological assays will further contact said oocytes with at least a partial inhibitor of ENaC, e.g., amiloride or an amiloride derivative as a control or in order to enhance measurable changes in sodium channel cell current.

In yet another preferred embodiment of the invention, frog oocytes that functionally express a human ENaC sodium channel are provided which express human ENaC alpha, beta and gamma or delata, beta and gamma subunits.

In another preferred embodiment of the invention, the ENaC used in cell-based assays according to the invention can be composed of naturally occurring human ENaC subunits, one or more alternatively spliced human ENaC subunits, or a functional variant thereof. Alternatively, the ENaC can be composed of at least the alpha subunit of a naturally occurring human ENaC, or an alternatively spliced version thereof. In another embodiment, a delta subunit (such as Genebank accession U38254; see *J Biol Chem*, 270(46):27411-4 (1995)) or a variant thereof can substitute for the alpha subunit.

Preferably, these subunits are encoded by SEQ ID: NO.: 1, 2, 3 and 7 disclosed infra. These and other aspects of the invention will become apparent to one of skill in the art from the following detailed description, drawings, and claims.

DETAILED DESCRIPTION OF THE DRAWINGS

FIG. 1 illustrates the functional expression of hENaC resulting in a sodium dependent amiloride sensitive fluorescence change. Transfection of HEK293T cells with varying 1:1:1 ratios of α, β, and γ, subunit plasmids of human kidney ENaC results in a $Na^+$ dependent amiloride sensitive voltage change, as compared to mock transfected cells. A, B, C, and D were transfected with 111:1 rations of α, β, and γ plasmid at absolute levels of 4.4.1, and 0.25 respectively. E and F were mock transfected with Beta-gal and pUC. Transfection efficiency was approximately 40% and cell density was approximately 70%. All traces are from a single plate with A (n=4), B, C, D, E (n=12), and F (n=8).

Figure 4:
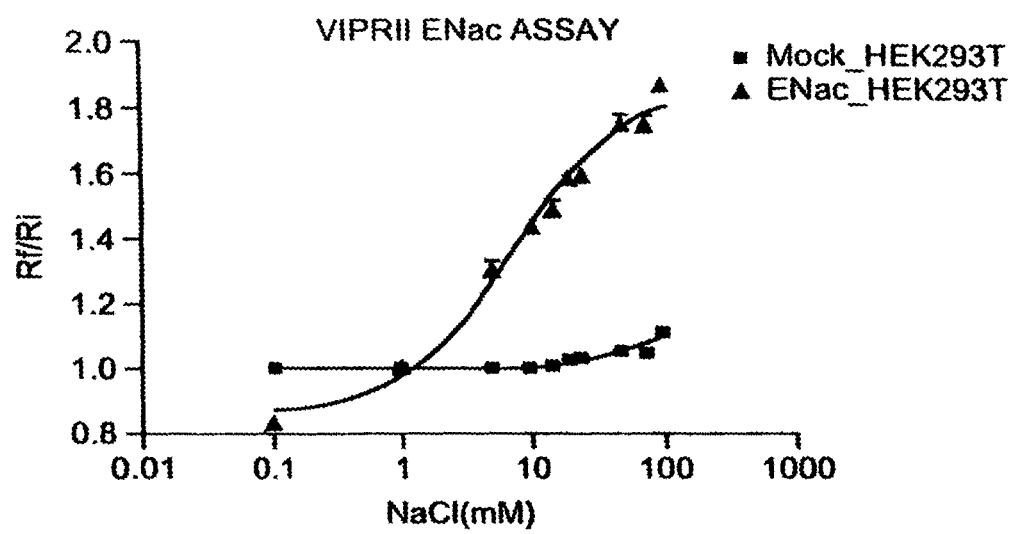

FIG. 4 illustrates the NaCl dose response relationship of HEK293T cells expressing ENaC using a voltage imaging plate reader (VIPR). HEK293T cells were transfected with ENaC subunits expression plasmids (ENaC) or a carrier plasmid (Mock). 24 hours later cells were loaded with a membrane potential dyes and changes in cell fluorescence in response to Na+ stimulation was monitored on VIPRII (Aurora Biosciences). Only cells expressing ENaC exhibited a change in response to increases in $Na^+$ concentration.

Figure 5:
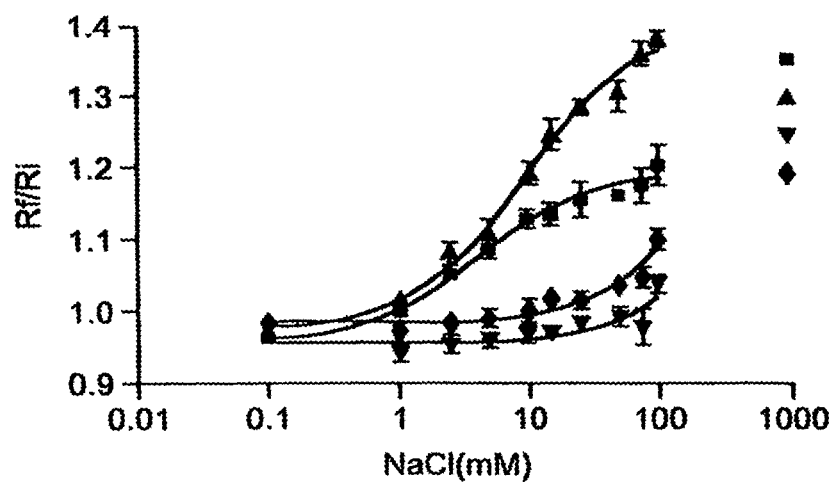

FIG. 5 also illustrates the NaCl dose response relationship of HEK2933T cells expressing human ENaC. HEK293T cells were transfected with ENaC subunits expression plasmids (ENaC) 24 hours later cells were loaded with a membrane potential dyes and changes in cell fluorescence in response to $Na^+$ stimulation was monitored on VIPRII (Aurora Biosciences). Phenamil, an ENaC antagonist, inhibited $Na^+$-induced changes in fluorescence. Conversely, the Compound "X", an ENaC enhancer, increased the $Na^+$-induced changes in fluorescence and this effect is inhibited by Phenamil.

Figure 6:
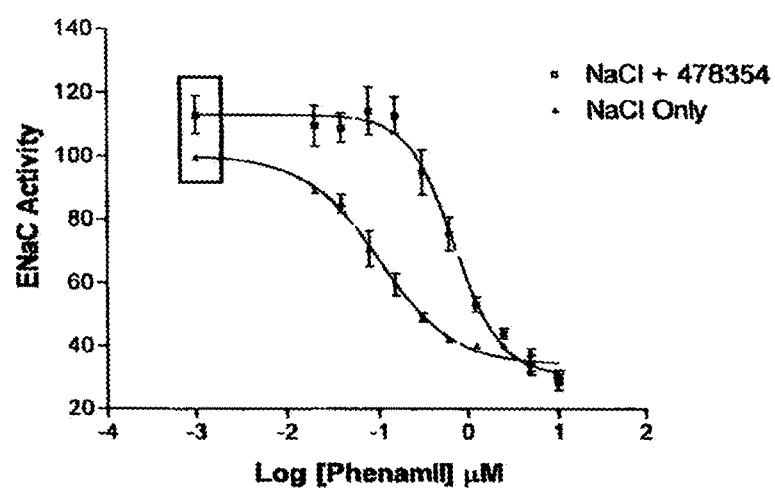

FIG. 6 shows the effect of increasing concentrations of Phenamil on ENaC activity. The blue trace: inhibition of ENC activity by Phenamil. Red trace: inhibition of ENC activity by Phenamil in the presence of 100 μM compound 478354, an ENaC enhancer. The black box contains data showing compound 478354's effect in the absence of Phenamil. The yellow box contains data showing enhanced 478354 effects by the presence of increasing concentrations of Phenamil.

Figure 7A:
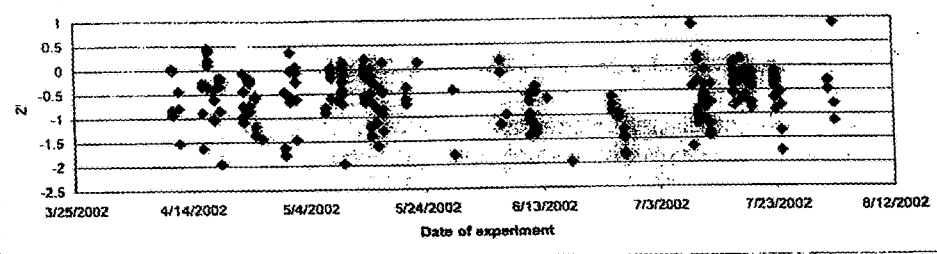

FIG. 7A. Distribution of Z' in the absence of Phenamil. "Z'" is defined as: 1-((3×standard deviation of ENaC responds to 3×standard deviation of ENaC response in the presence of compound 478354)/(mean ENaC activity in the presence of 478354-mean ENaC activity)). Most Z' values are less than 0 indicating that, when used in the high control, 479354 can not provide a meaningful assay window.

Figure 7B:
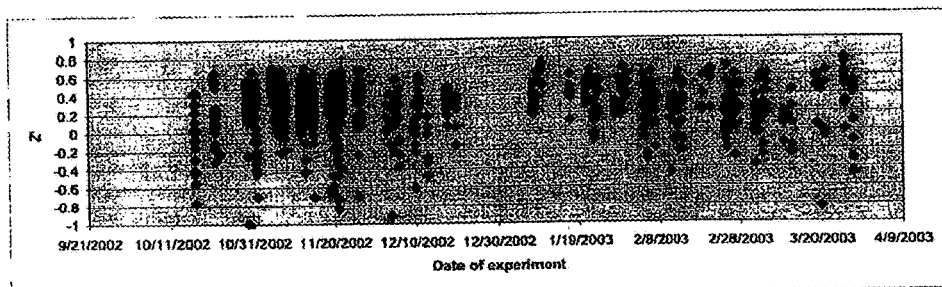

FIG. 7B. Distribution of Z' in the presence of 0.5 μM Phenamil. $Z^1$ is defined as: 1-((3×standard deviation of ENaC responds + 3×standard deviation of ENaC response in the presence of 478354)/(mean ENaC activity in the presence of 478354—mean ENaC activity)). Most $Z^1$ values are >0 and ≤1 indicating that as the high control, 478354 can provide a meaningful assay window in the presence of Phenamil.

FIG. 8 illustrates an example of screening oocytes injected with human ENaC cRNA for compounds that increase ENaC activity. For each compound screened, a % enhancement factor is calculated. This value corresponds to the magnitude of the current change due to compound divided by the magnitude of the current change due to amiloride multiplied by –100%. In this example, two compounds a re screened in succession in 7, out of a possible maximum 8, oocytes voltage clamped to –60 mV in the OpusXpress system. All 7 oocytes express ENaC, as evidenced by the inhibitory effect of amiloride on measured oocyte currents.

FIG. 9 illustrates an example of how the % enhancement factor is calculated for each oocyte injected with human ENaC cRNA. % enhancement factors are determined for each compound screened, averaged, and standard deviations determined. In this case, compound 1 and compound 2 correspond to the compounds screened in cells numbered 2 though 8 in FIG. 8.

FIG. 10 illustrates an example of screening oocytes not injected with human ENaC cRNA. Compounds have no effect on the activity Of ion channels expressed endogenously in the oocyte membrane, illustrating that compound activity is ENaC-dependent and attributable to increased macroscopic sodium current flowing through ENaC channels. Also the figure shows that amiloride has no effect on uninjected oocytes due to the absence of ENaC sodium channel expression.

FIGS. 11A and 11B illustrate examples of I/V curves in the oocytes injected with human ENaC cRNA or uninjected oocytes in the presence and absence of compound. In injected eggs, the compound increases the slope of the I/V curve, whereas in uninjected oocytes the compound has no effect on the slope of the I/V curve (i.e. the curves in the presence and absence of compound are identical).

FIG. 12 illustrates an example of an amiloride competition experiment in oocytes injected with human ENaC cRNA, co-application of amiloride plus compound does not enhance sodium currents flowing through ENaC channels. This indicates that compounds are working directly on the ENaC channel; when ENaC channels are closed due to amiloride, compounds cannot enhance ENaC function.

FIG. 13 illustrates an example of dose-response curves for 2 compounds in oocytes injected with human ENaC cRNA. Compound A is less potent than compound B as evidenced by its larger EC50 (5.4 uM with compound A compared to 0.47 uM with compound B) and right-shifted dose-response curve.

FIG. 14 schematically illustrates a set of experiments used to examine the effect of compounds on human ENaC activity in the oocyte expression system using the two-electrode voltage clamp (TEVC) technique.

DETAILED DESCRIPTION OF THE INVENTION

The present invention provides assay systems that comprise test cells, preferably recombinant mammalian cells or amphibian oocytes, that express a functional hENaC as well as mammalian cell-based and amphibian oocyte cell-based assays, preferably high or medium throughput, for the profiling and screening of an epithelial sodium channel (ENaC). More specifically, the invention provides human cell lines, e.g., HEK293T cells, and amphibian oocytes, that express the α, β, and γ subunits of hENaC that can be used in cell-based assays to screen for ENaC modulators. Also the invention provides mammalian cells and amphibian oocytes that express a functional ENaC comprised of delta, beta and gamma subunits for use in functionally characterizing ENaC activity, and to identify compounds that either enhance or block salty taste perception (herein referred to as salty taste modulators). These compounds can be used as ingredients in foods, medicinals and beverages to enhance, modulate, inhibit or block salty taste.

However, prior to discussing the invention in more detail the following definitions are provided. It should be otherwise understood that the technical terms and phrases have their ordinary meaning, as they would be construed by use of ordinary skill in the art.

Definitions

The term 'salty taste" or "salty taste perception" as used herein refers to a subject's perception or response to salt taste stimuli. As discussed above, it is believed that hENaC is involved in salty taste perception, in particular salts that elicit "a salty taste" in human subjects. Such stimuli include compounds such as NaCl that elicit a response in functional ENaCs, preferably hENaC.

The terms "ENaC" subunit protein or a fragment thereof, or a nucleic acid encoding one of three subunits of "ENaC" protein or a fragment thereof refer to nucleic acids and polypeptides, polymorphic variants, alleles, mutants, and interspecies homologues that: (1) have an amino acid sequence that has greater than a bout 80% amino acid sequence identity, 85%, 90%, preferably 91%, 92%, 93%, 94%, 95%, 96%, 97%, 98% or 99% or greater amino acid sequence identity, preferably over a region of over a region of at least about 25, 50, 100, 200, or 500, or more amino acids, to an amino acid sequence encoded by the nucleic acid sequence contained in SEQ ID NO:1; 2 or 3; or (2) specifically bind to antibodies, e.g., polyclonal antibodies, raised against an immunogen comprising an amino acid sequence encoded by SEQ ID NO:1, 2, or 7 or immunogenic fragments thereof, and conservatively modified variants thereof; or (3) specifically hybridize under stringent hybridization conditions to an anti-sense strand corresponding to a nucleic acid sequence encoding an ENaC protein, e.g., SEQ ID NO:1, 2, 3 or 7 or their complements, and conservatively modified variants thereof; or (4) have a nucleic acid sequence that has greater than about 80% sequence identity, 85%, 90%, preferably 91%, 92%, 93%, 94%, 95%, 96%, 97%, 98% or 99%, or higher nucleotide sequence identity, preferably over a region of at least about 25, 50, 100, 200, 500, 1000, or more nucleotides, to SEQ ID NO:1, 2, 3 or 7 or their complements, or (5) is functionally equivalent to the hENaC described herein in a sodium conductance assay when expressed in a HEK cell and tested by using two electrode whole cell electrophysiology or by the change in fluorescence of a membrane potential dye in response to sodium or lithium.

Functionally equivalent ENaC proteins include ENaC subunits with primary sequences different than those identified infra, but which possess an equivalent function as determined by functional assays, e.g., sodium conductance assays as described infra.

"Determining the functional effect" refers to assaying the effect of a compound that increases or decreases a parameter that is indirectly or directly under the influence of an ENaC polypeptide e.g., functional, physical and chemical effects. Such functional effects include, but are not limited to, changes in ion flux, membrane potential, current amplitude, and voltage gating, a as well as other biological effects such as changes in gene expression of any marker genes, and the like. The ion flux can include any ion that passes through the channel, e.g., sodium or lithium and analogs thereof such as radioisotopes. Such functional effects can be measured by any means known to those skilled in the art, e.g., by the use of two electrode electrophysiology or voltage-sensitive dyes, or by measuring changes in parameters such as spectroscopic characteristics (e.g., fluorescence, absorbance, refractive index), hydrodynamic (e.g., shape), chromatographic, or solubility properties. Preferably ENaC function will be evaluated by using two electrode whole cell electrophysiology or by monitoring the change in fluorescence of a membrane potential dye in response to sodium or lithium.

"Inhibitors", "activators", and "modulators" of ENaC polynucleotide and polypeptide sequences are used to refer to activating, inhibitory, or modulating molecules identified using cell-based assays of ENaC polynucleotide and polypeptide sequences. Inhibitors are compounds that, e.g., bind to, partially or totally block activity, decrease, prevent, delay activation, inactivate, desensitize, or down regulate the activity or expression of ENaC proteins, e.g., antagonists. "Activators" are compounds that increase, open, activate, facilitate, enhance activation, sensitize, agonize, or up regulate ENaC protein activity. Inhibitors, activators, or modulators also include genetically modified versions of ENaC proteins, e.g., versions with altered activity, as well as naturally occurring and synthetic ligands, antagonists, agonists, peptides, cyclic peptides, nucleic acids, antibodies, antisense molecules, ribozymes, small organic molecules and the like. Such assays for inhibitors and activators include, e.g., expressing ENaC protein in cells, cell extracts, or cell membranes, applying putative modulator compounds, and optionally prior thereto contacting said ENaC protein with a known ENaC inhibitor at a concentration that results in partial ENaC inhibitors and then determining the functional effects of the rotation compound on activity, as described above.

Samples or assays comprising ENaC proteins that are treated with a potential activator, inhibitor, or modulator are compared to control samples without the inhibitor, activator, or modulator to examine the extent of activation, inhibition or modulation. In one embodiment of the assay, compounds are tested for their effect on the response of cells provided with a suboptimal sodium concentration. Control cells, treated with the suboptimal concentration of sodium but lacking a compound, typically exhibit a 10-20% of the maximal response. Compounds that increase the response of the suboptimal sodium concentration above the 10-20% level are putative ENaC enhancers. In contrast, compounds that reduce the response to below 10% are putative ENaC enhancers.

The term "test compound" or "test candidate" or "modulator" or grammatical equivalents thereof as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid (e.g., a sphingolipid), fatty acid, polynucleotide, oligonucleotide, etc., to be tested for the capacity to modulate ENaC activity. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., enhancing activity, creating variants of the lead compound, and evaluating the property and activity of those variant compounds. Preferably, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

"Biological sample" includes sections of tissues such as biopsy and autopsy samples, and frozen sections taken for histologic purposes. Such samples include blood, sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

"Compound that inhibits ENaC activity" refers to a compound which inhibits sodium channel activity, preferably reversibly when this compound is contacted with a functional ENaC. Preferred examples of such compounds are amiloride and amiloride derivatives such as Phenamil, benzamil, $3^1$, $4^1$-dichlorobenzamil, ethylisopropylamiloride; 5-(N-4-chlorbenzyl)-$2^1$, $4^1$ dimethyl-benzamil, 5-(N-methyl-N-guanidinocarbonylmethyl) amiloride; 5-(N, N-hexa-myethylene) amiloride; 5-(N-ethyl-N-isopropyl) amiloride (EIPA); 5-(N-4-chloro-benzyl) $2^1$, $4^1$ dimethyl-benzamil, $2^1$, $4^1$-dimethylbenzamil; $2^1$, $3^1$-benzo-benzamil; and the like.

"Amiloride derivative" refers to a compound having a structure similar to amiloride which inhibits ENaC function. Typically such derivatives are substituted on the guanidine substituent (e.g., Phenamil) or on the 5-N position (e.g., ethylisopropylamiloride).

The terms "identical" or percent "identity," in the context of two or more nucleic acids or polypeptide sequences, refer to two or more sequences or subsequences that are the same or have a specified percentage of amino acid residues or nucleotides that are the same (i.e., about 80% identity, preferably 85%, 90%, 91%, 92%, 93%, 94%, 95%, 96%, 97%, 98%, 99%, or higher identity over a specified region (e.g., nucleotide sequences SEQ ID NO: 1, 2, 3 or 7), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site (www.ncbi.nlm.nih.gov) or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of an algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but those functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation, of a nucleic acid that encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologous, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan. (W); 7) Serine (S), Threonine (T); and 8) Cysteine (C), Methionine (M) (see, e.g., Creighton, *Proteins* (1984)). As noted previously, the invention embraces cells that express ENaC subunit polypeptides having primary sequences different than those disclosed in the subject application that are functionally equivalent in appropriate assays, e.g., using whole cell sodium conductance assays described in detail infra.

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered three-dimensional structures within a polypeptide. These structures are commonly known as domains, e.g., transmembrane domains pore domains, and cytoplasmic tail domains. Domains are portions of a polypeptide that form a compact unit of the polypeptide and are typically 15 to 350 amino acids long. Exemplary domains include extracellular domains, transmembrane domains, and cytoplasmic domains. Typical domains are made up of sections of lesser organization such as stretches of α-sheet and β-helices. "Tertiary structure" refers to the complete three-dimensional structure of a polypeptide monomer. "Quaternary structure" refers to the three dimensional structure formed by the noncovalent association of independent tertiary units. Anisotropic terms are also known as energy terms.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternatively polypeptides derived from the same nucleic acid by read-through transcription are also encompassed by this definition. Any products of a splicing reaction, including recombinant forms of the splice products, are included in this definition.

ENaC nucleic acid sequences also include single nucleotide polymorphisms which encode ENaC subunits that are functionally equivalent to the ENaC polypeptides disclosed herein when assayed using appropriate assays, in the sodium conductance assays described herein.

Membrane potential dyes or voltage-sensitive dyes refer to a molecule or combinations of molecules that change fluorescent properties upon membrane depolarization. These dyes can be used to detect the changes in activity of an ion channel such as ENaC expressed in a cell.

A "label" or a "detectable moiety" is a composition detectable by spectroscopic, photochemical, biochemical, immunochemical, chemical, or other physical means. For example; useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed, or not expressed at all. In the present invention this typically refers to cells that have been transfected with nucleic acid sequences that encode one or more ENaC subunits.

The term "heterologous" when used with reference to portions of a nucleic acid indicates that the nucleic acid comprises two or more subsequences that a re not found in the same relationship to e ach other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship, to each other in nature (e.g., a fusion protein). The term "heterologous" when used with reference to cellular expression of a gene, cDNA, mRNA or protein indicates that the gene, cDNA, mRNA, or protein is not normally expressed in the cell or is from another species than the original source of the cells.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. The wash and hybridization steps are generally carried out for ½, 1, 2, 5, 13, 15, 30, 60 or more minutes, and more typically for about 30 seconds to 2 minutes.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions o f similar stringency. Additional guidelines for determining hybridization parameters are provided in numerous reference, e.g., and *Current Protocols in Molecular Biology*, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to a bout 65° C., depending o n the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) PCR Protocols, A Guide to Methods and Applications, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

Particularly, such an antibody includes one which specifically binds to an ENaC disclosed herein, or a mixture of antibodies that specifically bind such ENaC polypeptides.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to ENaC subunit proteins, e.g., the ENaC alpha, beta, gamma or delta subunits as encoded by SEQ ID NO:1, 2, 3, or 7, polymorphic variants, alleles, orthologs, and conservatively modified variants, or splice variants, or portions thereof, can be selected to obtain only those polyclonal antibodies that are specifically immunoreactive with ENaC subunit proteins i.e., ENaC alpha, beta, gamma or delta subunits, e.g., those having the amino acid sequences contained in SEQ ID NO.: 4, 5, 6 or 8, and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

Assays for Proteins that Modulate ENaC activity

High or medium throughput functional genomics assays can be used to identify modulators of ENaC which block, inhibit, modulate or enhance salty taste. Such assays can, e.g., monitor changes in cell surface marker expression, changes in intracellular ions, or changes in membrane currents using either cell lines or primary cells or oocytes. Typically, the cells are contacted with a cDNA or a random peptide library (encoded by nucleic acids). The cDNA library can comprise sense, antisense, full length, and truncated cDNAs. The peptide library is encoded by nucleic acids. The effect of the cDNA or peptide library on the phenotype of the cells is then monitored, using an assay as described above. The effect of the cDNA or peptide can be validated and distinguished from somatic mutations, using, e.g., regulatable expression of the nucleic acid such as expression from a tetracycline promoter. cDNAs and nucleic acids encoding peptides can be rescued using techniques known to those of skill in the art, e.g., using a sequence tag.

Proteins interacting with the peptide or with the protein encoded by the cDNA (e.g., SEQ ID NO: 1, 2, or 7) can be isolated using a yeast two-hybrid system, mammalian two hybrid system, or phage display screen, etc. Targets so identified can be further used as bait in these assays to identify additional components that may interact with the ENaC channel which members are also targets for drug development (see, e.g., Fields et al., *Nature* 340:245 (1989); Vasavada et al., *Proc. Nat'l Acad. Sci. USA* 88:10686 (1991); Fearon et al., *Proc. Nat'l Acad. Sci. USA* 89:7958 (1992); Dang et al., *Mol. Cell. Biol.* 11:954 (1991); Chien et al., *Proc. Nat'l Acad. Sci. USA* 9578 (1991); and U.S. Pat. Nos. 5,283,173, 5,667,973, 5,468,614, 5,525,490, and 5,637,463).

Suitable cells and cell lines that express ENaC proteins include, by way of example, kidney epithelial cells, lung epithelial cells, taste epithelial cells and other mammalian epithelial cells, preferably human, and oocytes, preferably amphibian oocytes, most preferably *Xenopus* oocytes.

Isolation of Nucleic Acids Encoding ENaC Proteins

This invention relies, in part, on routine techniques in the field of recombinant genetics. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

Nucleic acids that encode ENaC subunits, polymorphic variants, orthologs, and alleles that are substantially identical to an amino acid sequence encoded by SEQ ID NO: 1, 2, 3 or 7 as well as other ENaC family members, can be isolated using ENaC nucleic acid probes and oligonucleotides under stringent hybridization conditions, by screening libraries. Alternatively, expression libraries can be used to clone ENaC subunit protein, polymorphic variants, orthologs, and alleles by detecting expressed homologous immunologically with antisera or purified antibodies made against human ENaC or portions thereof.

To make a cDNA library, one should choose a source that is rich in ENaC RNA. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263-269 (1983); Sambrook et al., supra; Ausubel et al., supra).

For a genomic library, the DNA is extracted from the tissue and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180-182 (1977). Colony hybridization is carried out as generally described in Grunstein et al., *Proc. Natl. Acad. Sci. USA,* 72:3961-3965 (1975).

Alternatively, ENaC cRNA encoding human ENaC subunits may be generated from α, β, γ or Δ human ENaC DNA plasmids using T7 RNA polymers to transcribe cRNA in vitro from DNA linearaized with appropriate restriction enzymes and the resultant cRNA microinjected into suitable cells, e.g., oocytes, preferably frog oocytes.

An alternative method of isolating ENaC subunit nucleic acid and its orthologs, alleles, mutants, polymorphic variants, and conservatively modified variants combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of human ENaC directly from mRNA, from cDNA, from genomic libraries or cDNA libraries. Degenerate oligonucleotides can be designed to amplify ENaC homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of ENaC encoding mRNA in physiological samples, for nucleic acid sequencing, or for other purposes. Genes amplified by the PCR reaction can be purified from agarose gels and cloned into an appropriate vector.

Gene expression of ENaC subunits can also be analyzed by techniques known in the art, e.g., reverse transcription and amplification of mRNA, isolation of total RNA or poly A$^+$ RNA, northern blotting, dot blotting, in situ hybridization, RNase protection, high density polynucleotide array technology, e.g., and the like.

Nucleic acids encoding ENaC subunit proteins can be used with high-density oligonucleotide array technology (e.g., GeneChip™) to identify ENaC protein, orthologs, alleles, conservatively modified variants, and polymorphic variants in this invention. In the case where the homologs being identified are linked to modulation of T cell activation and migration, they can be used with GeneChip™ as a diagnostic tool in detecting the disease in a biological sample, see, e.g., Gunthand et al., *AIDS Res. Hum. Retroviruses* 14: 869-876 (1998); Kozal et al., *Nat. Med.* 2:753-759 (1996); Matson et al., *Anal. Biochem.* 224:110-106 (1995); Lockhart et al., *Nat. Biotechnol.* 14:1675-1680 (1996); Gingeras et al., *Genome Res.* 8:435-448 (1998); and Hacia et al., *Nucleic Acids Res.* 26:3865-3866 (1998).

The genes encoding ENaC subunits preferably human ENaC subunits are typically cloned into intermediate vectors before transformation into prokaryotic or eukaryotic cells for replication and/or expression. These intermediate vectors are typically prokaryotic vectors, e.g., plasmids, or shuttle vectors.

1. Expression in Prokaryotes and Eukaryotes

To obtain high level expression of a cloned gene, such as those cDNAs encoding hENaC subunit, one typically subclones the hENaC subunit nucleic acid sequence into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al, supra. Bacterial expression systems for expressing the ENaC subunit protein are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, *Xenopus* oocytes and insect cells are well known in the art and are also commercially available.

In a preferred embodiment of the invention, an oocyte expression system is used to express a functional human ENaC and to examine the effects of specific compounds on sodium transport through ENaC channels. The *Xenopus* oocyte expression system has previously been used for the expression of ion channels, including ENaC, and in functional studies (Dascal, CRC Crit. *Rev. Biotech.* (1987) 22(4): 317-387; Wagner, et al., *Cellular Physiology and Biochemistry* (2000) 10:1-12; and Canessa et al., *Nature* (1994) 367:463-467). In still another embodiment retroviral expression systems may be used in the invention. In another embodiment transient expression systems may be utilized with plasmid-based vectors that are commercially available such as pcDNA 3 and derivatives thereof Selection of the promoter used to direct expression of a heterologous nucleic acid depends on the particular application. The promoter is preferably positioned about the same distance from the heterologous transcription start site, as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the ENaC subunit encoding nucleic acid in host c ells. A typical expression cassette thus contains at least one promoter operably linked to a nucleic acid sequence encoding a ENaC subunit(s) and signals required for efficient polyadenylation of the transcript, ribosome binding sites, and translation termination. Additional elements of the cassette may include enhancers and, if genomic DNA is used as the structural gene, introns with functional splice donor and acceptor site.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags may be included in an expression cassette for nucleic acid rescue. Markers such as fluorescent proteins, green or red fluorescent protein, β-gal, CAT, and the like can be included in the vectors as markers for vector transduction.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/A⁺, pMTO10/A⁺, pMAMneo-5, baculovirus pDSVE, and any other vector allowing expression of proteins under the direction of the CMV promoter, SV40 early promoter, SV40 late promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal.

In one embodiment, the vectors of the invention may have a regulatable promoter, e.g., tet-regulated systems and the RU-486 system (see, e.g., Gossen & Bujard, *PNAS* 89:5547 (1992); Oligino et al., *Gene Ther.* 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a ENaC encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods may be used to produce bacterial, mammalian, yeast or insect cell lines that express large quantities of ENaC protein, which are then purified using standard techniques (see, e.g., Colley et al., *J. Biol. Chem.* 264:17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, J. Bact. 132:349-351 (1977); Clark-Curtiss & Curtiss, *Methods in Enzymology* 101:347-362 (Wu et al., eds, 1983). Alternatively, in a preferred embodiment of the invention, oocytes that express human ENaC subunits are produced by microinjection of cRNA encoding said subunits therein.

Any of the well-known procedures for introducing foreign nucleotide sequences into host c ells may be used. These include the use of calcium phosphate transfection, polybrene, protoplast fusion, electroporation, biolistics, liposomes, lipids optimized for DNA transfection, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one ENaC subunit gene into a host cell, preferably mammalian capable of expressing functional ENaC.

After the expression vector is introduced into the cells, the transfected cells are cultured under conditions favoring expression of ENaC subunit(s). In one embodiment, the cells are transiently transfected with all three hENaC genes using lipid-based transfection and cultured for 24-48 hours prior to performing the screen for ENaC modulators.

As noted previously, a preferred embodiment of the invention comprises an oocyte expression system. Those methods generally include frog surgery, oocyte isolation, cRNA preparation and oocytes microinjection. General procedures for frog surgery and oocyte isolation are conventionally known in the art. (See, Marcus-Sekur, et al., *Methods in Enzymol.* 152:284-288 (1987); Goldin, *Methods in Enzymol.* 207:266-279.) Likewise, methods for preparing cRNA are also well known and are reported, e.g., in Swansen, et al., *Meth. Enzymol.* 207:310-319 (1912), Golden, et al., *Meth. Enzymol.*

217:279-297 (1992). The resultant cRNA is then microinjected into frog oocytes by standard methods. (See, Molten, et al., *Meth. Enzymol.* 254:458-466 (1975); Hitchcock et al., *Meth. Enzymol.* 152:276-284 (1987).

Assays for Modulators of ENaC Protein

A. Assays

Modulation of an ENaC protein can be assessed using a variety of assays; preferably cell-based models as described above. Such assays can be used to test for inhibitors and activators of ENaC, which modulate, block, enhance or inhibit salty taste perception.

Preferably, the ENaC will be comprised of three subunits, alpha (or delta), beta and gamma and preferably the human ENaC subunit encoded by the encoded by SEQ ID NO: 1, 2, 3 or 7 or a human ortholog a conservatively modified variant thereof. Alternatively, the ENaC of the assay will be derived from a non-human epithelial cell. Generally, the amino acid sequence identity of each respective subunit will be at least 80%, preferably at least 85%, or 90%, most preferably at least 95%, e.g., 96%, 97%, 98% or 99% to the polypeptide encoded by SEQ ID NO: 1, 2, 3 or 7.

Measurement of the effect of a candidate comprised or an ENaC protein or cell expressing ENaC protein, either recombinant or naturally occurring, can be performed using a variety of assays, as described herein. Preferably to identify molecules capable of modulating ENaC, assays are performed to detect the effect of various candidate modulators on ENaC activity in an amphibian oocyte or mammalian cell that expresses a functional ENaC. Preferably, such assays will initially contact ENaC with a known ENaC inhibitor prior to the addition of at least one putative ENaC modulator, e.g., ENaC enhancer. Preferably, the inhibitor will be amiloride or an amiloride derivative such as Phenamil.

The channel activity of ENaC proteins can be assayed using a variety of assays to measure changes in ion fluxes including patch clamp techniques, measurement of whole cell currents, radiolabeled ion flux assays, and fluorescence assays using voltage-sensitive dyes (see, e.g., Vestergarrd-Bogind et al., *J. Membrane Biol.* 88:67-75 (1988); Daniel et al., *J. Pharmacol. Meth.* 25:185-193 (1991); Hoevinsky et al., *J. Membrane Biol.* 137:59-70 (1994)) and ion-sensitive dyes. For example, nucleic acids encoding one or more subunits of an ENaC protein or homologue thereof can be injected into *Xenopus* oocytes. Channel activity can then be assessed by measuring changes in membrane current. One means to obtain electrophysiological measurements is by measuring currents using patch clamp techniques, e.g., the "cell-attached" mode, the "inside-out" mode, and the "whole cell" mode (see, e.g., Ackerman et al., *New Engl. J. Med.* 336:1575-1595, 1997). Whole cell currents can be determined using standard methodology such as that described by Hamil et al., *Pflugers. Archiv.* 391:185 (1981).

Channel activity is also conveniently assessed by measuring changes in intracellular ion levels for example using ion sensitive dyes.

The activity of ENaC polypeptides can be also assessed using a variety of other assays to determine functional, chemical, and physical effects, e.g., measuring the binding of ENaC polypeptides to other molecules, including peptides, small organic molecules, and lipids; measuring ENaC protein and/or RNA levels, or measuring other aspects of ENaC polypeptides, e.g., transcription levels, or physiological changes that affects ENaC activity. When the functional consequences are determined using intact cells or animals, one can also measure a variety of effects such as changes in cell growth or pH changes or changes in intracellular second messengers such as IP3, cGMP, or cAMP, or components or regulators of the phospholipase C signaling pathway. Such assays can be used to test for both activators and inhibitors. Modulators thus identified are useful for, e.g., as flavorants in foods, beverages and medicines.

Cell-Based Assays

In another embodiment, at least one ENaC subunit protein is expressed in a cell, and functional, e.g., physical and chemical or phenotypic, changes are assayed to identify ENaC modulators. Cells expressing ENaC proteins can also be used in binding assays. Any suitable functional effect can be measured, as described herein. For example, changes in membrane potential, changes in intracellular ion levels, and ligand binding are all suitable assays to identify potential modulators using a cell based system. Suitable cells for such cell-based assays include both primary cells, e.g., taste epithelial cells that expresses an ENaC protein and cultured cell lines such as HEK293T cells that express an ENaC. Another preferred expression system will comprise amphibian oocytes. As noted, these assays will preferably initially contact the ENaC expression cell line, e.g., amphibian oocytes or HEK293 with a known ENaC inhibitor, e.g., amiloride or an amiloride derivative such as Phenamil at a concentration that partially inhibits ENaC function, prior to contacting the cell line with at least one putative ENaC modulator. The ENaC protein can be naturally occurring or recombinant. Also, as described above, fragments of ENaC proteins or chimeras with ion channel activity can be used in cell based assays.

In yet another embodiment, cellular ENaC polypeptide levels are determined by measuring the level of protein or mRNA. The level of ENaC protein or proteins related to ENaC ion channel activation are measured using immunoassays such as western blotting, ELISA and the like with an antibody that selectively binds to the ENaC polypeptide or a fragment thereof. For measurement of mRNA, amplification, e.g., using PCR, LCR, or hybridization assays, e.g., Northern hybridization, RNase protection, dot blotting, is preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, ENaC expression can be measured using a reporter gene system. Such a system can be devised using an ENaC protein promoter operably linked to a reporter gene such as chloramphenicol acetyltransferase, firefly luciferase, bacterial luciferase, β-galactosidase and alkaline phosphatase. Furthermore, the protein of interest can be used as an indirect reporter via attachment to a second reporter such as red or green fluorescent protein (see, e.g., Mistili & Spector, *Nature Biotechnology* 15:961-964 (1997)). The reporter construct is typically transfected into a cell. After treatment with a potential modulator, and preferably prior thereto treatment with a known ENaC inhibitor, e.g., Phenamil, the amount of reporter gene transcription, translation, or activity is measured according to standard techniques known to those of skill in the art.

In another embodiment, a functional effect related to signal transduction can be measured. An activated or inhibited ENaC will alter the properties of target enzymes, second messengers, channels, and other effector proteins. Assays for ENaC activity include cells that are loaded with ion or voltage sensitive dyes to report channel activity, e.g., by observing membrane depolarization or sodium influx. Assays for determining activity of such receptors can also use known antagonists for ENaC, such as amiloride or phenamil, as controls to assess activity of tested compounds. In assays for identifying modulatory compounds (e.g., agonists, antagonists), changes in the level of ions in the cytoplasm or membrane potential will be monitored using an ion sensitive or membrane potential fluorescent indicator, respectively. Among the ion-sensitive indicators and voltage probes that may be employed are those disclosed in the Molecular Probes 2002 Catalog: (www.probes.com). and specific compounds disclosed infra.

A preferred assay system will use frog oocytes injected with ENaC cRNAs which are contacted with a test compound and then analyzed by the two-electrode voltage clamp electrophysiological recording technique. (See Stuhmer, *Meth. Enzymol.* 207:319-339 (1992); Wagner et al., *Cellular Physiology and Biochemistry* 10:1-12 (2000)).

Electrophysiological Assay

As noted, a preferred assay for identification of compounds that modulate, i.e., enhance, inhibit or block ENaC comprises an electrophysiological assay that monitors changes in electrical current in cells that express human ENaC subunits that are contacted with at least one putative ENaC modulator (enhancer or inhibitor). These assays may use any cell that expresses a functional ENaC. In the preferred embodiment, the cells will comprise oocytes, preferably frog oocytes, mammalian cells, yeast cells or insect cells, or another expression system that is suitable for expressing a functional ENaC ion channel. Preferably, the expression system will exhibit robust and rapid human ENaC sodium channel expression and desirably will not express any or very few endogenous ion channels, thereby facilitating the identification of compounds that specifically modulate ENaC sodium channel function. Thereby, an undesirable background response is minimized or eliminated. Moreover, robust cells, such as oocytes, are desirable as this enables the cells to be reused in assays according to the invention. Oocytes have been reported previously to rapidly and robustly express other functional ion channels including ENaCs (Pascal, CRC Crit. Rev. Biotech. 22(4):317-87 (1987); Wagner et al., *Cell Physiol. Biochem.* 10:1-12 (2000); Canessa et al., *Nature* 367:463-467 (1994)).

A particularly preferred electrophysiological assay is a moderate throughput assay that measures ENaC sodium channel function in frog oocytes by the two-electrode voltage clamp technique. This robust, fast expression system provides for the expression of ~1 million ENaC channels in an oocyte membrane after only about 18-24 hours. Moreover, because oocytes are relatively large (1 mm in diameter, relatively large compared to most mammalian cells), they are easy to handle and work with.

Based on these advantages, a single oocyte can be used to obtain multiple and repetitive electrophysiological recording. Also, an oocyte typically expresses few endogenous channels, and expression is at levels below that which cause high background relative to the background seen in some other expression systems, e.g., HEK293T cells. Thereby, oocytes allow for repeated direct measurement of the effect of target compounds on ENaC sodium channel function.

In a preferred two-electrode voltage clamp assay according to the invention (exemplified in detail in the Example 4 infra), frog oocytes that have been microinjected with ENaC α, β, and γ human ENaC cRNAs (or δ, β and γ) human ENaC cRNAs) are transferred to glass scintillation vials and incubated under appropriate conditions to facilitate ENaC protein expression.

After ENaC sodium ion channel expression is obtained, typically around 24 hours post-cRNA microinjection, ENaC function is measured according to the two-electrode voltage clamp technique using an appropriate two-electrode voltage measuring device, e.g., OpusXpress 6000A parallel oocyte voltage clamp system (Axon Instruments). The two-electrode voltage clamp technique measures the macroscopic electrical current flowing across the entire oocyte membrane through the ENaC sodium ion channels. Oocytes are punctured with a voltage-sensing electrode and a current sensing electrode; the voltage, or potential difference across the oocyte membrane, is clamped to a particular value using the voltage-sensing electrode and the current, or the flow of ions across the oocyte membrane, required to maintain the voltage is measured using the current-sensing electrode. The OpusXpresss system is one example of a commercially available two-electrode voltage measuring device which is semi-automated and which comprises a workstation that permits electrophysiological recordings to be made from 8 oocytes simultaneously. This system also provides for automated oocyte impalement and delivery of target compounds by a computer-controlled fluid handler that delivers compound into 96-well compound plates. This system can best be described as a medium or moderate-throughput system as it allows for the evaluation of about 60 compounds per week. Of course more compounds can be screened by the addition of other voltage measuring devices, as described.

In this assay system, ENaC enhancers will result in an increase in current passing through the ENaC channels in the oocyte membrane. This value is calculated by a standard formula provided infra in (Example 4). Such assays also may include appropriate negative controls, e.g., amiloride, which is a known ENaC inhibitor that blocks sodium transport through ENaC channels. Therefore, this compound functions both as an internal control to verify that oocytes express functional ENaC, and, in oocytes exhibiting amiloride inhibition, allows for the screening of putative ENaC enhancers after amiloride compound is applied (if the target compound is an ENaC enhancer it will result in an increase in current passing through ENaC channels in the oocyte membrane).

Desirably, a % enhancement factor is calculated for each enhancer. For example, a 100% enhancer increases ENaC activity 100% relative to the basal control value (no compound).

Negative controls are also desirably performed to confirm that oocytes which are not injected with ENaC cRNAs do not exhibit the same effects.

As discussed in greater detail in Example 4 infra, more complex analyses are also desirably performed on compounds that exhibit maximal % enhancement valves e.g., current/voltage (I/V) curves, amiloride competitive experiments and dose-response curves to determine the concentration at which the compound exhibits half-maximal activity (EC50 value). These experiments will further confirm that the effect of the compound is ENaC-specific.

These assays will provide for the identification of ENaC modulators, preferably ENaC enhancers, which may be used as additives for foods, beverages, pharmaceuticals and the like in order to modulate the salty taste associated therewith. Desirably, an ENaC enhancer will exhibit at least 20% enhancement factor, more preferably at least 50% and even more preferably at least an 100% enhancement factor. These oocyte-based assays are discussed in further detail as well as the intrinsic advantages associated therewith in Example 4 of this application.

Animal Models

Animal models that express hENaC also find use in screening for modulators of salty taste. Similarly, transgenic animal technology including gene knockout technology, for example as a result of homologous recombination with an appropriate gene targeting vector, or gene overexpression, will result in the absence or increased expression of the ENaC protein. The same technology can also be applied to make knockout cells. When desired, tissue-specific expression or knockout of the ENaC protein may be necessary. Transgenic animals generated by such methods find use as animal models of responses to salty taste stimuli.

Knockout cells and transgenic mice can be made by insertion of a marker gene or other heterologous gene into an endogenous ENaC gene site in the mouse genome via homologous recombination. Such mice can also be made by substituting an endogenous ENaC with a mutated version of the ENaC gene, or by mutating an endogenous gene.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., Science 244:1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987).

B. Modulators

The compounds tested as modulators of ENaC protein can be any small organic molecule, or a biological entity, such as a protein, e.g., an antibody or peptide, a sugar, a nucleic acid, e.g., an antisense oligonucleotide or a ribozyme, or a lipid. Alternatively, modulators can be genetically altered versions of an ENaC protein. Typically, test compounds will be small organic molecules, peptides, lipids, and lipid analogs. Preferably, the tested compounds are safe for human consumption.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including ChemDiv (San Diego, Calif.), Sigma-Aldrich (St. Louis, Mo.), Fluka Chemika-Biochemica-Analytika (Buchs Switzerland) and the like.

In the preferred embodiment, moderate or high throughput screening methods involve providing a small organic molecule or peptide library containing a significant number of potential ENaC modulators (potential activator or inhibitor compounds). Such "chemical libraries" are then screened in one or more assays, as described herein, to identify those library members (particular chemical species or subclasses) that display a desired characteristic activity. The compounds thus identified can serve as conventional "lead compounds" or can themselves be used as potential or actual products. As noted, the preferred oocyte two-voltage clamp electrode system (a single device) permits about 60 compounds to be tested per week.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)):. Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random biooligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274: 1520-1522 (1996) and U.S. Patent 5,593,853), small organic molecule libraries (see, e.g., benzodiazepines, Baum C&EN, Jan. 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

Foods and Beverage Compositions Containing ENaC Modulatory Compound Identified Using Disclosed Assays The compounds identified using the disclosed assays, e.g., the electrophysiological (two electrode voltage-clamp technique) assays and fluorescence cell-based assay disclosed in the examples, are potentially useful as ingredients or flavorants in ingestible compositions, i.e., foods and beverages as wells as orally administered medicinals. Compounds that modulate or enhance salty taste perception can be used alone or in combination as flavorants in foods or beverages. In the preferred application, the modulator will be incorporated into a food or beverage with a reduced level of sodium and the salty taste of the resulting product will be similar to that of the high sodium product. Examples of such foods and beverages include snack foods such as pretzels, potato chips, crackers, soups, dips, soft drinks, packaged meat products, among others.

Alternatively, compounds that block or inhibit salty taste perception can be used as ingredients or flavorants in foods that naturally contain high salt concentrations in order to block or camouflage the salty taste thereof.

The amount of such compound(s) will be an amount that yields the desired degree of salty taste perception. Of course compounds used in such applications will be determined to be safe for human consumption and to be acceptable in human taste tests.

Preferred Assay Embodiment Using Phenamil or Equivalent

As disclosed supra, one of the preferred embodiments of the invention will comprise contacting a test cell expressing a functional ENaC with at least one putative modulator compound in the presence of a membrane potential dye, and preferably prior thereto contacting said test cell with at least one compound known to modulate (inhibit) ENaC function, preferably an amiloride derivative such as Phenamil and monitoring the activity of the ENaC expressed by the test cell to determine the extent of ENaC modulation. As noted, the addition of an ENaC inhibitor prior to the test compound improves assay results. This inhibitor, e.g., Phenamil, is used at a concentration that at least partially inhibits ENaC function. The method can further comprise evaluating the putative modulator compound for in vivo effects on salty taste perception (e.g., performing tasting experiments to determine the in vivo effect on salty taste perception). For example, cDNAs encoding the ENaC subunits are cloned from human kidney cell cDNA, human lung cell cDNA, or human taste cell cDNA. As mentioned above, native ENaC is a multimeric protein consisting of three subunits (alpha or delta, beta, and gamma). ENaC functions as a constitutively active $Na^+$ selective cation channel, is found in taste buds as well as other tissues, and is a candidate human salt receptor underlying the physiological perception of salty taste.

In another preferred embodiment of the invention, such a method is carried out in a high throughput assay format using multi-well plates and a fluorescence intensity plate reader (e.g., Aurora Biosciences VIPR instrument or Molecular Device's FLIPR instrument). The test cells may be seeded, dye-loaded, optionally, preferably initially contacting the test cells with a known ENaC inhibitor at a concentration whereby ENaC function is at least partially and preferably reversibly inhibited, thereafter contacting said test cell with at least one test compound, and monitoring fluorescence intensity in the same multi-well plate. Such an assay format can reliably detect both activation or inhibition of ENaC function, providing a robust screen for compounds that could either enhance or block channel activity. The assay described above has been optimized to identify ENaC enhancers. The assay described herein thus has advantages over existing assays, such as those described above, in that a human ENaC is utilized, mammalian cells are employed and the assay can be run in standard multi-well (e.g., 96, 384, or 1536 well) plates in high-throughput mode. (However, as discussed above, mammalian cells possess some disadvantageous properties, e.g., they may express endogenous ion channels at levels resulting in undesirable background levels.)

In this preferred embodiment of the invention, cells, preferably mammalian cells, will be produced that functionally express at least the alpha (or delta) subunit of ENaC. In preferred embodiments, all three subunits of hENaC ($\alpha$ or $\delta$, $\beta$, and $\gamma$) are expressed either transiently or stably. The ENaC subunit(s) employed can be naturally occurring forms, variants containing SNPs, alternatively spliced forms, combinations of forms or any functional variants known in the art (see e.g., accession numbers P37088, P51168, P51170, and P51172). Preferably, the ENaC will be comprised of the human alpha, beta and gamma ENaC subunits encoded by the nucleic acid sequence in SEQ ID NO. 1, 2, 3 or the human beta, gamma and delta ENaC subunits encoded by SEQ ID NO. 2, 3 and 7. The mammalian cells can be any type known in the art such as COS, CHO, BHK, MDCK, HEK293, or HEK293T (human embryonic kidney cells expressing the large T-cell antigen). Preferably, the cell is HEK293T. The cells can be transfected using standard methods known in the art, such as but not limited to $Ca^{2+}$ phosphate or lipid-based systems, or methods previously mentioned.

These transfected cells are then preferably seeded into multi-well culture plates. Functional expression is then allowed to proceed for a time sufficient to reach at least about 70% confluence, more preferably to at least about 80% confluence or to form a cell layer dense enough to withstand possible fluid perturbations caused by compound addition. Generally, an incubation time of at least 24 hours will be sufficient, but can be longer as well. The cells are then washed to remove growth media and incubated with a membrane-potential dye for a time sufficient to allow the dye to equilibrate across the plasma membranes of the seeded cells. One of skill in the art will recognize that the dye loading conditions are dependent on factors such as cell type, dye type, incubation parameters, etc. In one embodiment, the dye may be used at about 2 µM to about 5 µM of the final concentration. Further, the optimal dye loading time may range from about 30 to about 60 minutes at 37° C. for most cells. In the preferred embodiment, the membrane potential dyes are from Molecular Devices (cat# R8034). In other embodiments, suitable dyes include e.g., single wavelength-based dyes such as DiBAC, DiSBAC (Molecular Devices), and Di-4-ANEPPS (Biotium), or dual wavelength FRET-based dyes such as DiSBAC2, DiSBAC3, and CC-2-DMPE (Aurora Biosciences). [Chemical Names—Di-4-ANEPPS (Pyridinium, 4-(2-(6-(dibutylamino)-2-naphthalenyl)ethenyl) -1-(3-sulfopropyl)-, hydroxide, inner salt), DiSBAC4(2) (bis-(1,2-dibarbituric acid)-trimethine oxanol), DiSBAC4(3) (bis-(1,3-dibarbituric acid)-trimethine oxanol), CC-2-DMPE (Pacific Blue™ 1,2-ditetradecanoyl-sn-glycero-3-phosphoethanolamine, triethylammonium salt) and SBFI-AM (1,3-Benzenedicarboxylic acid, 4,4'-[1,4,10-trioxa-7,13-dia-zacyclopentadecane-7,13-diylbis(5-methoxy-6,12-benzofurandiyl)] bis-, tetrakis[(acetyloxy)methyl] ester].

In one embodiment, the dye-loaded cells are preferably contacted with a known ENaC inhibitor, e.g., Phenamil, then contacted with test compounds (or controls), and the cell cultures are monitored using standard fluorescence analysis instrumentation such as or VIPR or FLIPR®. The addition of NaCl or other test compounds which pharmacologically act on ENaC elicit a change in membrane potential which is then detected as a change in the resting fluorescence in a standard fluorescence intensity plate reader (e.g., FLIPR) or voltage intensity, plate reader (e.g. VIPR). As such, the method of the present invention can be used to identify salty taste modulating compounds by monitoring the activity of ENaC in the test cells through fluorescence. For instance, a decrease in fluorescence may indicate a taste (salty) blocker, while an increase in fluorescence may indicate a taste (salty) enhancer.

Having generally described the invention, the same will be more readily understood by reference to the following examples, which are provided by way of illustration and are not intended as limiting. It is understood that various modifications and changes can be made to the herein disclosed exemplary embodiments without departing from the spirit and scope of the invention.

EXAMPLE 1

DNA sequences encoding the alpha, beta and gamma subunit of a human ENaC expressed in human taste cells were cloned from human kidney cells by RT-PCR.

Methods for Cloning Human Epithelium Sodium Channel Subunit DNA Sequences (ENaCs)

Human ENaC cDNAs for α, β and γ ENaC were amplified from human kidney cDNA (Origene Technologies Inc.) by PCR using the following primer pairs, respectively: 5' CGC GGATCC GCC CAT ACC AGG TCT CAT G 3' and 5' CCG GAATTC CTG CAC ATC CTT CAA TCT TGC 3'; 5' CGC GGATCC AGC AGG TGC CAC TAT GCA C 3' and CCG CTCGAG GTC TTG GCT GCT CAG TGA G 3'; 5' CGC GGATCCCCT CAA AGT CCC ATC CTC G 3'and 5' CCG GAATTC GAC TAG ATC TGT CTT CTC AAC 3'. The primers were designed to be complementary to 5' and 3'-untranslated region sequence in order to retain the endogenous translation initiation signal, and they introduced terminal restriction endonuclease sites that were used to clone amplified ENaC cDNAs into the mammalian expression vector pcDNA3 (Invitrogen) for functional expression experiments. The cloned ENaC cDNAs were sequenced and compared to ENaC sequences in public DNA databanks. Each cloned subunit is a composite of polymorphisms present in different databank alleles; that is, every polymorphism in each cloned subunit identified by pairwise comparison of the cloned subunit to a databank allele could be found in another databank allele. In addition, polymorphisms in cloned ENaC subunits were verified by sequencing of cloned cDNAs amplified in independent PCR experiments.

Figure 1:
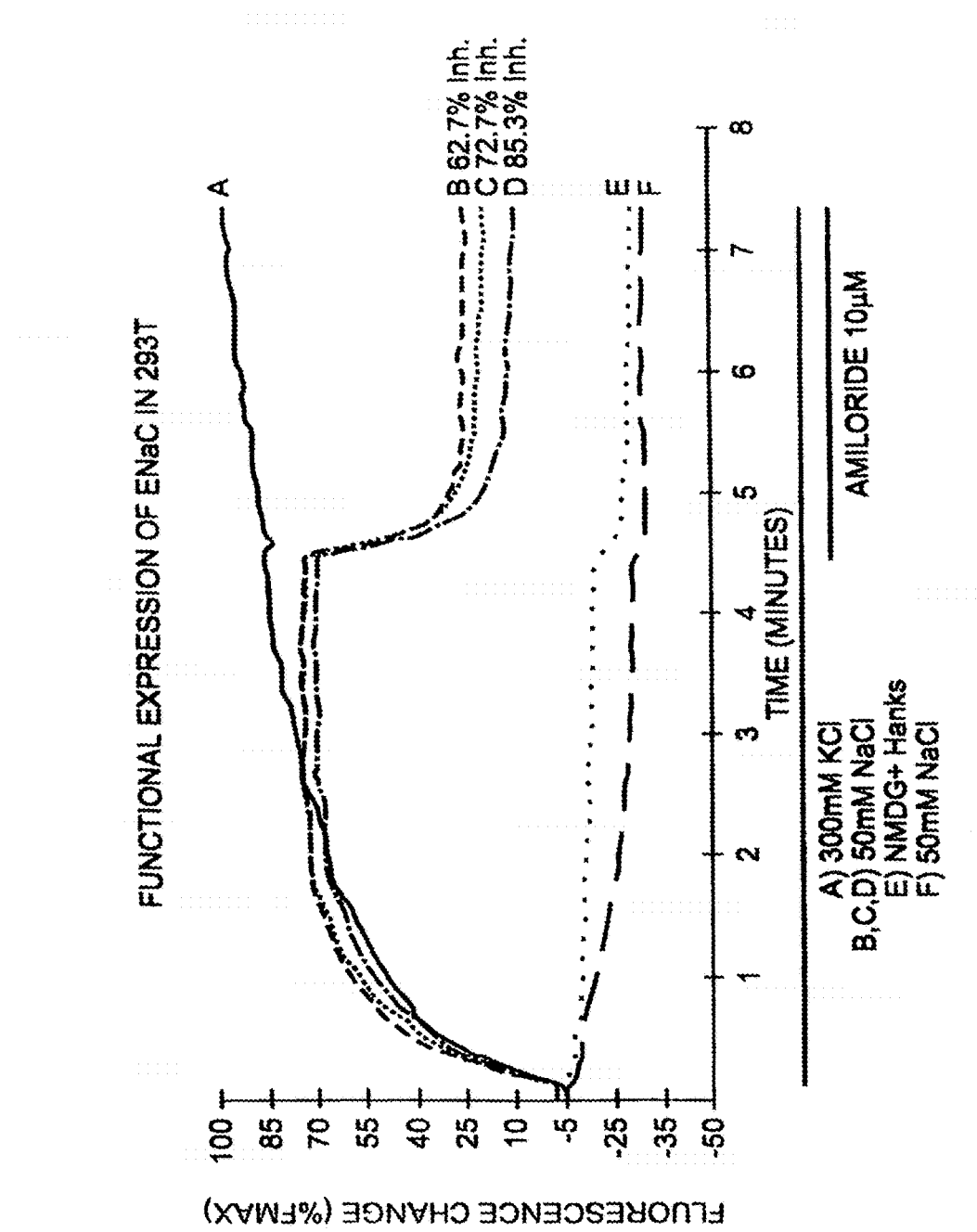

The nucleic acid sequences encoding cloned sequences alpha, beta and gamma hENaC subunits are respectively contained in SEQ ID NO: 1, SEQ ID NO: 2 and SEQ ID NO: 3 and the corresponding amino acid _10 sequences in SEQ ID NO: 4, 5 and 6. Each of these DNA sequences was inserted into the expression vector pcDNA3 to produce alpha, beta and gamma subunit plasmids that express human ENaC subunit polypeptides. Also, the nucleic acid sequence for the human amiloride sensitive sodium channel delta subunit (ΔNaCh) is contained in SEQ ID NO: 7, which functions equivalently to the ENaC alpha subunit. The amino acid sequence for the delta subunit is contained in SEQ ID NO: 8. HEK293T cells were transiently transfected via $Ca^{2+}$ phosphate with 1:1:1 weight ratios of α, β, and γ subunit plasmids expressing human ENaC. Such transfection resulted in a $Na^+$ dependent amiloride sensitive fluorescence change, as compared to mock-transfected cells. With reference to FIG. 1, samples A, B, C, and D were transfected with 1:1:1: ratios of α, β, and γ subunit plasmids at absolute levels of 4, 4, 1, and 0.25 micrograms, respectively. Samples E and F were mock transfected with Beta-gal and pUC DNAs. Transfection efficiency was approximately 40% and cell density was approximated 70%. Cells were analyzed using a FLIPR I (Molecular Devices) instrument using a membrane-potential fluorescent dye. All traces shown are from a single plate with A (n=4), B, C, D, E, (n=12), and F (n=8).

Figure 2A:
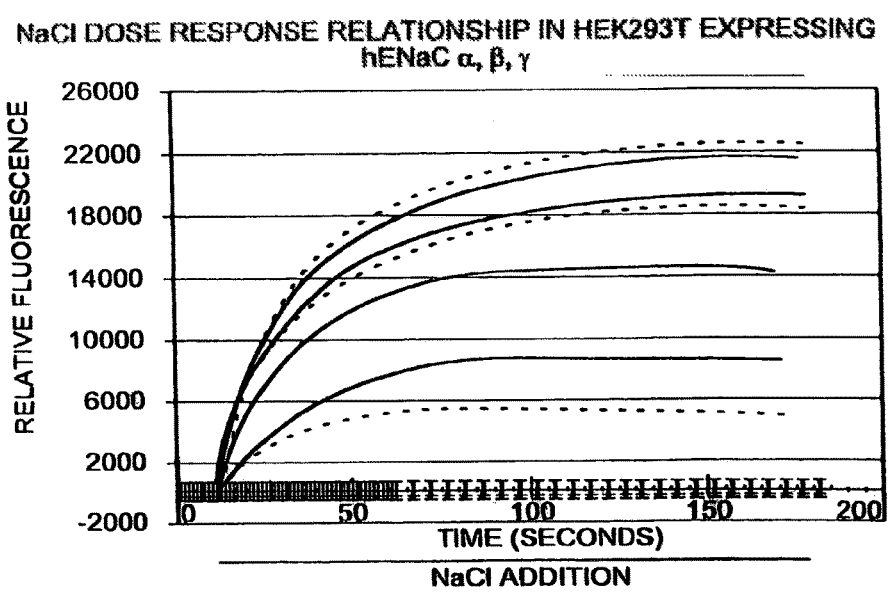
FIGS. 2A and 2B illustrate the NaCl dose response relationship of HEK293Tcells expressing hENaC α, β, and γ.
Figure 2B:
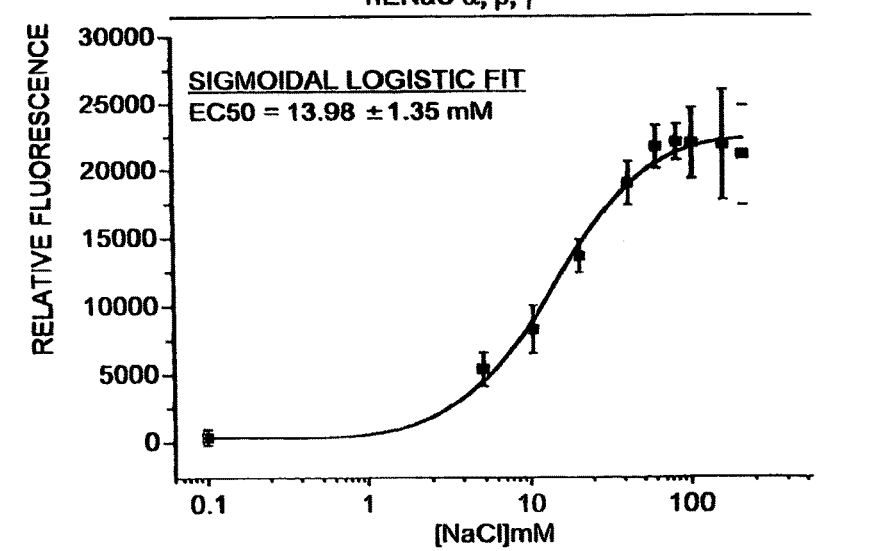
Figure 3A:
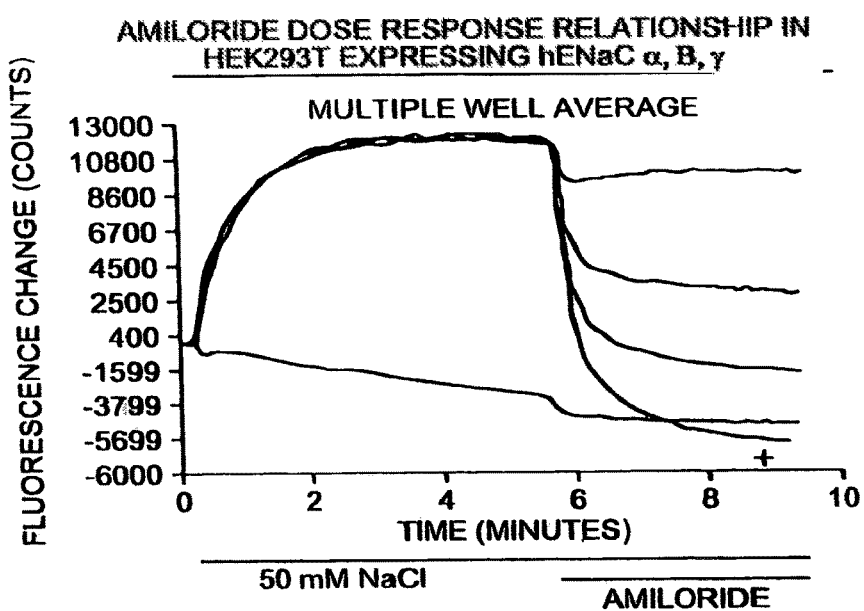
FIGS. 3A and 3B illustrate the amiloride dose response relationship of HEK293Tcells expressing hENaC α, β, and γ treated with 50 mM NaCl.
Figure 3B:
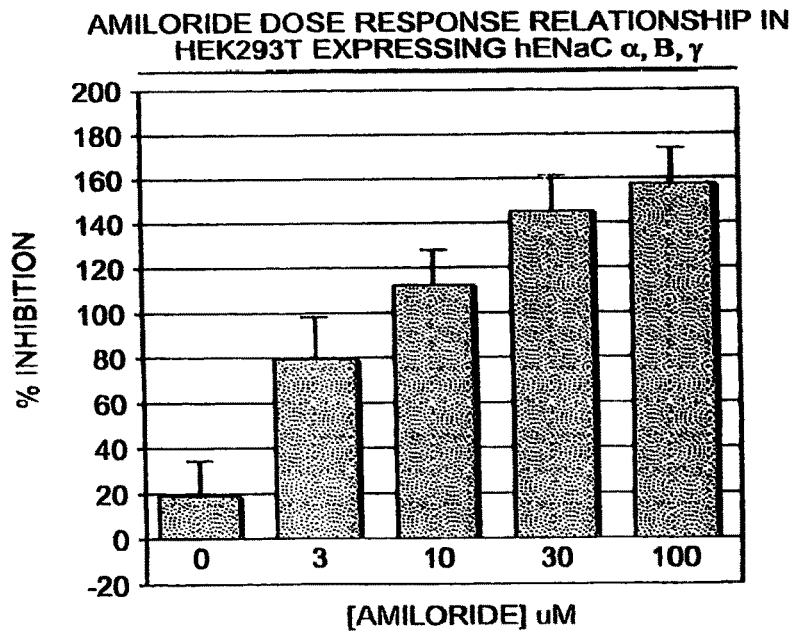

As depicted in FIGS. 1, 2, and 3, sodium-dependant amiloride-sensitive changes in resting potential (hENaC responses) were not significantly affected in untransfected HEK293T cells. Further, such resting potential changes were greatly enhanced in cells transfected with all three subunits of the hENaC compared to cells transfected with only the alpha subunit of hENaC (data not shown). Moreover, the ability of NaCl to induce membrane potential changes, and the effect of amiloride to block hENaC channel activity follow dose response-relationships similar to that reported in the literature using low throughput electrophysiological recording.

EXAMPLE 2

DNA sequences encoding the alpha, beta and gamma subunits of a human ENaC, SEQID 1, 2, and 3, respectively, were each cloned into the expression vector pcDNA3 to produce alpha, beta and gamma subunit plasmids that express human ENaC subunit polypeptides. HEK293T cells were transiently transfected via lipofection with 1:1:1 weight ratios of α, β, and γ subunit plasmids expressing human ENaC (2 µg of each subunit/20 million cells). Transfected cells were plated into 384-well plates and analyzed on a VIPRII Instrument (Aurora Biosciences) using voltage-sensitive fluorescent dyes. Cells expressing ENaC exhibited a $Na^+$ dependent fluorescence change, as compared to mock-transfected cells (FIG. 1). In FIG. 2, the $Na^+$-dependent fluorescence change is totally abolished by Phenamil, a known ENaC antagonist. Conversely, another compound was found to increase the $Na^{+-}$dependent fluorescence change but this effect is abolished by Phenamil. This compound is believed to be an ENaC enhancer, as it acts opposite to Phenamil in this assay for ENaC function.

Methods and Materials for Example 2:
1. All materials used are identified below in the "Materials Section".
2. HEK293T cells are grown to 80% confluence and dissociated from the culture dishes with an enzymatic solution (Trypsin/EDTA) for 3 minutes at 37C. Detached cells are analyzed for density and viability using a bench top flow cytometer (Guava; Guava Technologies). Cells with less than 85% viability are discarded from the experiment.
    [The procedures herein are conditions for transfection of HEK293T cells equivalent to ten screening 384-well plates (200,000,000 cells). These conditions can be altered e.g., by increasing or decreasing cell confluency by use of different size multi-well plates etc.]
3. Dissociated cells are washed and recovered in their culture medium (complete) at a density of ~1,000,000 cells/ml. Mammalian expression plasmid DNAs encoding the human ENaC subunits are mixed in an eppendorf in an equal ratio (10 ug α; 10 ug β and 10 ug γ/20,000,000 cells). 170 µg of carrier plasmid DNA (pUC-18) is then added to the DNA mix (for a total of 200 µg DNA/200,000,000 cells). 557 ul of the transfection reagent TransIT (Panvera Corporation) is added to 20 ml of culture medium exempt of serum and antibiotic. The DNA solution is then added to the Transit solution and the DNA-lipid solution is incubated at room temperature. After 60 minutes, the DNA-lipid complexes are transferred into the cell solution and volume is adjusted to 320 ml with complete cell culture medium for a final density of 635,000 viable cells/ml. (As discussed previously, the alpha subunit DNA may be interchanged with the delta subunit DNA and used to produce recombinant cells that express a functional ENaC comprised of the beta, gamma and delta ENaC subunits.)
4. Black 384-well poly-D-lysine clear bottom screening plates (Becton Dickinson) are coated with 40 µl/well of a Matrigel solution (20 µg/ml; Collaborative Biomedical Products) for 1 hour at room temperature. Coating solution is removed and plates are kept at room temperature until cell plating.
5. The cell/DNA solution is plated with a Multidrop into 384 well plates at a density of 50,000 cells/well (80 µl/well).
6. 27 hours after plating, cells are washed and loaded with the membrane potential sensitive dyes (CC2-DMPE and DiSBAC2(3)) as described below.
7. Cells are stimulated with 200µM compounds ([2×]) and read on line using a Voltage Intensity Plate Reader (VIPRII; Aurora Biosciences Corporation). Other concentrations of compounds can be used in the assay. Buffer preparation and plate layout are described below in the VIPR. The assay is performed at "room temperature", typically about 22° C., but can also be performed at other temperatures by preheating or cooling the cells and reagents prior to addition of compounds.

Materials
1. HEK 293T cells growing on 150 cm² flask (Becton Dickinson 0.2 um vented Blueplug seal cap) (37° C., 6% $CO_2$)
2. Dulbecco's Modified Eagle Medium (DMEM) (cat #11965-092 Gibco BRL) (Kept at 4° C.)
3. DMEM with HEPES (DMEMH) (cat #12430-054, Gibco BRL) (Kept at 4° C.)
4. Foetal Bovine serum (FBS) (cat#10082-147, Gibco BRL) (Kept in −20° C.)
5. Trypsin EDTA (1×) (cat#25200-072 Gibco-BRL) (Kept in −20° C.)
6. TransIT-293 (cat#MIR2705, Panvera) (Kept in 4° C.)
7. α, β, and γ ENaC DNA preparations (1 µg/µL each) (Kept in 4° C.)
8. pUC18 carrier DNA ((1 µg/µL) (Kept at 4° C.)
9. Matrigel (cat #40230, Collaborative Biomedical Products)
2. Cell Loading HBSS - Hank's Buffered Saline Solution
$DiSBAC_2(3)$                    5 mM in 100% DMSO        2.5 µM
ESS-CY4 or VABSC-1         200 mM in $dH_2O$                350 µM
VIPR NMDG BUFFER - see formula in "VIPR Plate Layout" section below:

| Components | 10 ml | To Make Volume 50 ml | 100 ml | 200 |
|---|---|---|---|---|
| CC2-DMPE(µ) | 20 | 100 | 200 | 400 |
| Pluronic(µ) | 20 | 100 | 200 | 400 |
| HBSS(ml) | 10 | 50 | 100 | 200 |
| $DiSBAC_2(3)(µ)$ | 5 | 25 | 50 | 100 |
| ESS(µ) | 17.5 | 87.5 | 175 | 350 |
| VIPR NMDG Buffer(ml) | 10 | 50 | 100 | 200 |

Preparation of CC2-DMPE Loading Buffer
1. Mix equal volumes of the CC2-DMPE stock solution and Pluronic F127.
2. Add the CC2-DMPE/Pluronic mix to HBSS while vortexing.

Loading of cells with CC2-DMPE
1. Remove cells from $CO_2$ incubator.
2, Look for variation of density/well
3. Prime EMBLA with HBSS 4. Wash c ells with H BSS 3×80 ul to remove residual growth medium and serum
5. Add 40 μL of 10 μM CC2-DMPE loading buffer to each well
6, Look for variation of density/well
7. Incubate for 30 minutes at room temperature in the dark.

Preparation of DiSBAC$_2$(3) loading buffer (can be done during CC2 incubation)
1. Mix DiSBAC$_2$(3) and ESS-CY4or VABSC-1, plus double volume of PluronicF127 of DiSBAC2(3)
2. Add the above mix to VIPR NMDG BUFFER, vortex Loading of cells with DiSBAC2(3) loading buffer
1. Prime EMBLA with NMDG buffer
2. Wash CC2-DMPE-loaded cells using VIPR NMDG buffer as the wash buffer, 3×80 μ/well
3. Add 40μ of 2.5 μM DiSBAC2(3), 350 μM ESS-CY4 or VABSC-1 loading buffer to each well
4. Look for variation of density/well
5. Incubate for 20 minutes at room temperature in the dark before running on VIPR II

VIPR Plate Layout

ENaC VIPR compound plate preparation 384 well format

Prepare enough of the following buffers to load all plates:

| Stock Solutions: | | NMDG Buffer: | NaCl Buffer: | High K Buffer | "VIPR NONE BUFFER" |
|---|---|---|---|---|---|
| | Final | 130 mM NMDG | 150 mM NaCl | 160 mM KCl | 2 mMKCl |
| | | 2 mM KCL | 2 mM KCL | 2 mM CaCl2 | 2 mMCaCl2*2 H2O |
| | | 2 mM CaCl2 | 2 mM CaCl2 | 1 mM MgCl2 | 1 mMMgCl2*6 H20 |
| | | 1 mM MgCl2 | 1 mM MgCl2 | 10 mM Hepes | 10 mMHEPES acid |
| | | 10 mM Hepes | 10 mM Hepes | 5 mMD-glucose | 5 mM D-glucose |
| | | 5 mM D-glucose | 5 mM D-glucose | | pH 7.3 w/ Trisbase |

| | | |
|---|---|---|
| Pluronic F127 | 100 mg/ml in 100% DMSO | |
| DiSBAC₂(3) | 5 mM in 100% DMSO | 2.5 μM |
| ESS-CY4 or VABSC-1 | 200 mM in dH₂0 | 350 μM |
| VIPR NMDG BUFFER | | |
| VIPR Na+ BUFFER | | |
| VIPR High K buffer | | |

| Final Volume | 10 mls | 15 mls | 20 mls | 100 mls | 200 mls | 400 mls | 500 mls |
|---|---|---|---|---|---|---|---|
| DiSBAC₂(3) (μl) | 5 | 7.5 | 10 | 50 | 100 | 200 | 250 |
| ESS or VABSC-1 (μl) | 17.5 | 26.25 | 35 | 175 | 350 | 700 | 875 |
| Pluronic F127 | 10 | 15 | 20 | 100 | 200 | 400 | 500 |

Preparation of Column 1 top half Buffer
1. Mix DiSBAC2(3) and ESS-CY4 or VABSC-1 and Pluronic F127 into VIPR NMDG buffer while vortex
Preparation of Column 1 bottom half Buffer
1. Mix DiSBAC2(3) and ESS-CY4 or VABSC-1 and Pluronic F127 into VIPR HighK buffer while vortex
Preparation of Column 24 buffer
Add VIPR NMDG buffer into Column 24

-continued

VIPR Plate Layout

| Preparation of Column 2_23 70 mM NaCl loading buffer | | | | | | | | | | | 70 mM NaCl | NaCl Buffer: | NMDG Buffer: |
|---|---|---|---|---|---|---|---|---|---|---|---|---|---|
| 1. Mix VIPR Na+buffer with VIPR NMDG buffer to make 70mM NaCl | | | | | | | | | | | 30 mls | 14 | 16 |
| 2. Mix DiSBAC2(3) and ESS-CY4 or VABSC-1 and Pluronic F127 into the above buffer while vortex | | | | | | | | | | | 300 mls | 140 | 160 |
| | | | | | | | | | | | 460 mls | 214.6 | 245.3 |

Adding 2 μl of 100% DMSO into Column 1, 2 and 24
Adding 2 μl of 10 nM compound X in 100% DMSO to Column 23
Adding all the other compound into Column 3_22.

| Plate layout | 1 | 2 | 3,4 | 5,6 | 7,8 | 9,10 | 11,12 | 13,14 | 15,16 | 17,18 | 19,20 | 21,22 | 23 | 24 |
|---|---|---|---|---|---|---|---|---|---|---|---|---|---|---|
| A | NMDG | 70 mMNaCl | 70 mMNaCl | 70 mMNaCl + all the compounds | | | | | | | | | 70 mM Na + 200 μM XNMDG |
| B | NMDG | 70 mMNaCl | 70 mMNaCl | | | | | | | | | | | 70 mM Na + 200 μM XNMDG |
| C | NMDG | 70 mMNaCl | 70 mMNaCl | | | | | | | | | | | 70 mM Na + 200 μM XNMDG |
| D | NMDG | 70 mMNaCl | 70 mMNaCl | | | | | | | | | | | 70 mM Na + 200 μM XNMDG |
| E | NMDG | 70 mMNaCl | 70 mMNaCl | | | | | | | | | | | 70 mM Na + 200 μM XNMDG |
| F | NMDG | 70 mMNaCl | 70 mMNaCl | | | | | | | | | | | 70 mM Na + 200 μM XNMDG |
| G | NMDG | 70 mMNaCl | 70 mMNaCl | | | | | | | | | | | 70 mM Na + 200 μM XNMDG |
| H | NMDG | 70 mMNaCl | 70 mMNaCl | | | | | | | | | | | 70 mM Na + 200 μM XNMDG |
| I | HighK | 70 mMNaCl | 70 mMNaCl | | | | | | | | | | | 70 mM Na + 200 μM XNMDG |
| J | HighK | 70 mMNaCl | 70 mMNaCl | | | | | | | | | | | 70 mM Na + 200 μM XNMDG |
| K | HighK | 70 mMNaCl | 70 mMNaCl | | | | | | | | | | | 70 mM Na + 200 μM XNMDG |
| L | HighK | 70 mMNaCl | 70 mMNaCl | | | | | | | | | | | 70 mM Na + 200 μM XNMDG |
| M | HighK | 70 mMNaCl | 70 mMNaCl | | | | | | | | | | | 70 mM Na + 200 μM XNMDG |
| N | HighK | 70 mMNaCl | 70 mMNaCl | | | | | | | | | | | 70 mM Na + 200 μM XNMDG |
| O | HighK | 70 mMNaCl | 70 mMNaCl | | | | | | | | | | | 70 mM Na + 200 μM XNMDG |
| P | HighK | 70 mMNaCl | 70 mMNaCl | | | | | | | | | | | 70 mM Na + 200 μM XNMDG |

EXAMPLE 3

Improved ENaC Assay Using ENaC Inhibitor (Phenamil)

Modulation of ENaC functions is monitored in human embryonic kidney (HEK)293 cells expressing the three different ENaC subunits. HEK293 cells are transiently transfected with the ENaC subunit plasmids using lipid-based systems. Transfected HEK293 cells are seeded into 384-well screening plates and functional expression of ENaC is allowed to proceed for a total of 24 hours. Cells are then labeled with specific dyes (such as DisBac2(3) and CC2-DMPE, Panvera) allowing the detection in subtle changes in membrane potential. Changes in dye fluorescence properties, upon modulation of ENaC functions, are monitored using a Voltage-Intensity-Plate-Reader (VIPR, Panvera). Using this technology, we can detect inhibition of ENaC function (Na+-induced change in membrane potential dye fluorescence) with increasing concentration of a known ENaC inhibitor, Phenamil (FIG. 6, blue trace). On the other hand an ENaC enhancer (ID # 478354) increases ENaC activity by roughly 18% (FIG. 6, difference between red and blue data points in the black rectangle). Notably, the effect of compound 478354 is greatly improved by increasing concentrations of Phenamil (FIG. 6, difference between the red and blue data points in yellow rectangle). Under these conditions, 478354 increases ENaC activity by as much as 50-60% in the presence of 0.2 to 0.5µM Phenamil. We conducted more than 241 and 835 independent experiments in the absence and presence of 0.5 µM Phenamil respectively (FIGS. 7A and 7B). During these experiments, we determined the effect of 478354 on the assay window using a Z' factor. Z' is a statistical parameter used to judge the quality of a signal window by quantifying the separation of high and low controls sets with respect to their variance. A Z'≥0 and indicates a meaningful signal window by which tested chemistries can be compared during screening. In the absence of Phenamil, a signal window determined by the 478354 high control standard failed in more than 90% of experiments (FIG. 2A). However, in the presence of Phenamil, 478354 significantly increased the signal window in 85% of experiments, with most of the Z' centered around 0.26 (FIG. 2B).

These results indicate that the use of an ENaC inhibitor such as Phenamil, prior to screening with one or more potential ENaC modulators, e.g., ENaC enhancers, enhances signal intensity, thereby significantly improving the likelihood of identifying molecules enhancing ENaC activity in throughput cell-based assays.

EXAMPLE 4

Electrophysiological Assay for Identifying ENaC Modulators Using Amphibian Oocytes that Express Functional Human ENaC The oocyte expression system has intrinsic advantages (expression levels, robust, low endogenous ion channel expression, et al.) that render it useful to examine the effects of compounds on sodium transport through ENaC channels. These compounds are candidates for enhancing salt taste perception. The oocyte expression system has been used earlier for the rapid and robust expression of ion channels, including ENaC, in functional studies (Dascal, CRC Crit. Rev. Biochem. (1987) 22(4): 317-387; Wagner, et al, Cellular Physiology and Biochemistry (2000) 10: 1-12; Canessa, et al, Nature (1994) 367: 463-467). Therefore, this system was selected for use in a two-electrode voltage clamp assay using methods and materials as described below.

The oocyte expression system is comprised of the following steps and methodologies, which collectively comprise the screen for ENaC enhancers: frog surgery and oocyte isolation, cRNA preparation, oocyte microinjection, and measurement of ENaC currents in oocytes using two-electrode voltage clamp electrophysiological recordings. The following references describe general practices for frog surgery and oocyte isolation (Marcus-Sekura, et al, Methods in Enzymology (1987) 152: 284-288; Goldin, Methods in Enzymology (1992) 207: 266-279), cRNA preparation (Swanson, et al, Methods in Enzymology (1992) 207: 310-319; Goldin, et al, Methods in Enzymology (1992) 207: 279-297), oocyte microinjection (Matten, et al, Methods in Enzymology (1995) 254: 458-466; Hitchcock, et al, Methods in Enzymology (1987) 152: 276-284), and two-electrode voltage clamp electrophysiological recording (Stuhmer, Methods in Enzymology (1992) 207: 319-339; Wagner, et al, Cellular Physiology and Biochemistry (2000) 10: 1-12). Each of these methodologies, as they pertain to the screen for ENaC enhancers, is described in further detail below.

Frog Surgery and Oocyte Isolation

Female *Xenopus laevis* South African clawed frogs greater than or equal to 9 cm in length are obtained from NASCO (Fort Atkinson, Wis.). Frogs are anesthetized in 0.15% MS-222 (tricaine or ethyl-3-aminobenzoate methanesulfonate; Sigma) in distilled water and placed on ice. Using sterile surgical tools, sequential 1-2 cm incisions are made in the abdomen through both the outer skin layer and the inner peritoneal layer. Excised ovarian lobes (containing 1000-2000 oocytes) are placed in OR-2 calcium-free media (82.5 mM NaCl, 2 mM KCl, 1 mM $MgCl_2$, 5 mM HEPES pH 7.5 with NaOH) and sequentially digested with 2 mg/ml collagenase type IA (Sigma), prepared immediately before use, for 45 min followed by 1 mg/ml collagenase type IA for 15 min on a rocking platform at room temperature. After enzymatic digestion, at which point the majority of oocytes are released from the ovarian lobes, oocytes are rinsed in OR-2 without collagenase and transferred to a Petri dish containing Barth's saline (88 mM NaCl, 2 mM KCl, 0.82 mM $MgSO_4$, 0.33 mM $Ca(NO_3)2$, 0.41 mM $CaCl_2$, 2.4 mM $NaHCO_3$, and 5 mM HEPES pH7.5; Specialty Media) supplemented with 2.5 mM sodium pyruvate. Mature stage V or VI oocytes (~1 mm diameter) containing distinct animal poles, corresponding to the dark side of the egg containing melanin pigment granules, and vegetal poles, corresponding to the light side of the egg containing yolk proteins, are selected for microinjection Frogs are sutured using a C6 needle with a 3-0 black braid suture (Harvard Apparatus) and reused for oocyte isolation following a 2-3 month recovery period.

cRNA Preparation

ENaC cRNA is generated using the mMESSAGE mMACHINE kit according to the manufacturer's instructions (Ambion) from α, β, and γ human ENaC DNA plasmids described in our previous patent (PCT WO 02/087306 A2) using T7 RNA polymerase to transcribe cRNA in vitro from DNA linearized with Eco RI for αand γENaC and linearized with Xho I for β ENaC. cRNA quality is checked by denaturing agarose gel electrophoresis and spectrophometric absorbance readings at 260 and 280 nm to ensure that full-length, non-degraded cRNA is generated.

Microinjection

Microinjection needles are pulled on a Model P-97 Flaming/Brown Micropipette Puller (Sutter Instrument Co.) using borosilicate glass capillaries (World Precision Instruments Inc.), back-filled with mineral oil (Sigma), and then front-filled with ENaC cRNA using a Nanoliter 2000 injector with a Micro4 MicroSyringe Pump Controller (World Precision Instruments). Oocytes are microinjected in the animal pole with 10-15 nl containing 1-3 ng of each α, β, and γ human ENaC cRNA. Following microinjection, oocytes are transferred to glass scintillation vials containing Barth's solution supplemented with 2.5 mM sodium pyruvate and incubated at 18-19° C. overnight under normal atmospheric conditions. During this time, the oocytes translate injected ENaC cRNA into protein.

Measurement of ENaC Currents in Oocytes Using Two-Electrode Voltage Clamp Electrophysiological Recordings Twenty-four hours post-microinjection, ENaC function is measured in oocytes using the two-electrode voltage clamp technique on an OpusXpress 6000A parallel oocyte voltage clamp system (Axon Instruments). The two-electrode voltage clamp technique is an electrophysiology method that measures the macroscopic electrical current flowing across the entire oocyte membrane though protein channels such as ENaC (Stuhmer, Methods in Enzymology (1992) 207: 319-339). Oocytes are impaled with a voltage-sensing electrode and a current-sensing electrode; the voltage, or potential difference across the oocyte membrane, is clamped to a particular value using the voltage-sensing electrode and the current, or the flow of ions across the oocyte membrane, required to maintain that voltage is measured using the current-sensing electrode. The OpusXpress system is a semi-automated two-electrode voltage clamp workstation that allows recordings to be made from 8 oocytes simultaneously. Oocyte impalement is automated and compound delivery is performed by computer-controlled fluid handlers from 96-well compound plates. This medium-throughput system dramatically increases the number of compounds we can examine from ~1 compound per week using a conventional single oocyte voltage clamp system to ~60 compounds per week using the OpusXpress system.

Oocytes are placed in the OpusXpress system and bathed in ND-96 solution (96 mM NaCl, 2.5 mM KCl, 1 mM $CaCl_2$, 1 mM $MgCl_2$, and 5 mM HEPES pH 7.5 with NaOH). Oocytes are impaled with voltage-sensing and current-sensing electrodes, pulled on a Model P-97. Flaming/Brown Micropipette Puller (Sutter Instrument Co.) using borosilicate glass capillaries (World Precision Instruments Inc.) and back-filled with 3M KCl, containing silver chloride wires. Electrodes exhibit resistances between 2-10 Mohm for voltage-sensing electrodes and between 0.5-2 Mohm for current-sensing electrodes. Following impalement, oocytes are voltage clamped to −60 mV and experimental recordings are initiated. Data are acquired at 50 Hz and low-pass filtered at 5 Hz using a 4-pole Bessel filter.

A preferred procedure used to screen a compound for ENaC enhancement in an oocyte assay according to the invention is as follows (FIG. 8). First, amiloride is applied (1 uM; Sigma). Amiloride is an inhibitor that blocks sodium transport through ENaC channels and is used as an internal control to verify that the oocytes express functional ENaC protein (Canessa, et al, Nature (1994) 367: 463-467). Second, in oocytes exhibiting amiloride inhibition, evidenced by a decrease in current flowing across the oocyte membrane following amiloride treatment, a compound is applied (concentration between ~0.1 uM and ~100 uM). If the compound functions as an ENaC enhancer, the current passing through ENaC channels in the oocyte membrane increases. To quantitate the effect of a compound on ENaC function, we use the following formula: $[(A-Ao)/(B-Bo)] \times -100$, where A is the current following compound treatment, Ao is the current preceeding compound treatment, B is the current following amiloride treatment, and Bo is the current preceeding amiloride treatment (FIG. 8). This value leads to a % enhancement factor that is used to gauge the activity of compounds in our assay. For example, if the % enhancement factor is equal to 100%, then the compound increases ENaC activity 100% over basal control values (in the absence of compound). % enhancement factors are calculated individually for each of the oocytes in the OpusXpress system and then an average and standard deviation are determined for each compound (FIG. 9).

Negative control experiments are performed in oocytes not injected with ENaC cRNA to demonstrate that effects observed with compounds in ENaC expressing oocytes are due to currents flowing through ENaC channels and not due currents flowing through channels endogenously expressed in the oocyte membrane. (Dascal, CRC Crit. Rev. Biochem. (1987) 22(4): 317-387). Compounds specifically enhancing ENaC should not affect currents in uninjected oocytes and should exhibit % enhancement factors of 0 (FIG. 10).

More complex analyses are performed on compounds displaying large % enhancement factors and having no effect on oocytes not injected with ENaC cRNA. The assays include current/voltage (I/V) curves, amiloride competition experiments, and dose-response curves. For I/V curves, currents are measured in voltage steps from −100 to +60 mV, in 20 mV increments, in the presence and absence of amiloride, to verify ENaC expression as above, and in the presence and absence of compound, to investigate the magnitude of compound enhancement (FIG. 11). All non-ENaC currents (defined as currents not blocked by amiloride) are substracted and I/V curves are plotted. The slope of the I/V curve is indicative of the magnitude of current enhancement by the compound of interest. Strong enhancers exhibit I/V curves with a large positive slope. In addition, the x-intercept of the I/V curve is indicative of what type of ion is being transported in two-electrode voltage clamp experiments. For sodium ion transport, the x-intercept falls within the range of 10-40 mV, depending on the degree of sodium loading in the oocytes. In oocytes not injected with ENaC cRNA, I/V curves performed in the presence of compound should be identical and superimpossible with I/V curves performed in the absence of compound (FIG. 11).

Amiloride competition experiments are desirably performed to demonstrate that compound effects are ENaC dependent (FIG. 12). First, amiloride is applied as above to demonstrate ENaC expression in the oocytes. Then, compound is applied to determine the % enhancement factor. Finally, amiloride and compound are co-applied. For an enhancer to work directly on the ENaC channel, co-application of amiloride plus compound should exhibit an amiloride phenotype, meaning that currents are inhibited and not enhanced. This assay shows that when the ENaC channel is closed, due to amiloride, the compound cannot have an enhancing effect; therefore, the compound must directly modulate ENaC channel function.

Dose-response curves are performed to determine the concentration at which the compound exhibits half-maximal activity (EC50) (FIG. 13). The lower the EC50, the more active the compound is as an ENaC enhancer. Dose-response curves are performed by sequentially applying increasing concentrations of enhancer starting from low doses (~1 nM) and progressing to high doses (~1 mM). % enhancement factors are calculated as described above and plotted as a function of compound concentration on a logarithmic scale to determine an EC50 value for the compound.

A flowchart which schematically illustrates the sequence of experiments performed to examine the effect of a compound on ENaC function is depicted in FIG. 14, including screening at a holding potential of −60 mV, I/V curves, amiloride competition tests, dose-response curves, and testing uninjected oocytes.

Analysis of Results

In our previous patent application (PCT WO 02/087306 A2), we utilized a high-throughput mammalian cell-based assay in HEK293T human embryonic kidney cells that indirectly measured ENaC activity by assaying membrane voltage in ENaC-transfected cells loaded with voltage-sensitive fluorescent probes. Although this approach was high-throughput, and identified some compounds that modulated ENaC, unfortunately, it was not specific, and ~90% of identified compounds did not directly modulate ENaC function but instead likely modulated the activity of other ion channels endogenously expressed in HEK293T cells. The efficacy of such high throughput assays is improved herein by the use of phenamil and similar ENaC inhibitors as described supra. In addition, the subject application also provides a more direct (specific), but lower throughput assay methodology to measure ENaC sodium channel function in oocytes using the two-electrode voltage clamp technique. This system allows rapid and robust expression of ion channels (~1 million ENaC channels can be expressed in the oocyte membrane after only about 18-24 hours). Other advantages of the oocyte expression system include: oocytes are large (~1 mm in diameter) and robust making them easy to handle and work with; multiple and repetitive recordings can be obtained from the same oocyte to the same or different compounds of interest; oocytes express few endogenous channels at levels sufficient to cause high background current in comparison to the current stemming from an exogenously expressed ion channel; and oocytes allow direct measurement of ion channel function. Thus, in contrast to assays that indirectly measure ENaC function in HEK293T cells using voltage-sensitive probes, the oocyte expression system allows direct measurement of ENaC sodium channel current with virtually no background.

Nucleic Acid and Amino Acid Sequences of ENaC Subunits Used in Examples

```
Length 2010 nucleotides
DNA
Human hENaC alpha clone #3-1-1 coding sequence
                                             SEQ ID NO: 1
atggaggggaacaagctggaggagcaggactctagccctc cacagtccactccagggctcatgaaggggaacaagcgtga ggagcaggggctggccccgaacctgcggcgccccagcag cccacggcggaggaggaggccctgatcgagttccaccgct cctaccgagagctcttcgagttcttctgcaacaacaccac catccacggcgccatccgcctggtgtgctcccagcacaac cgcatgaagacggccttctgggcagtgctgtggctctgca cctttggcatgatgtactggcaattcggcctgcttttcgg agagtacttcagctaccccgtcagcctcaacatcaacctc aactcggacaagctcgtcttccccgcagtgaccatctgca ccctcaatccctacaggtacccggaaattaaagaggagct ggaggagctggaccgcatcacagagcagacgctctttgac ctgtacaaatacagctccttcaccactctcgtggccggct cccgcagccgtcgcgacctgcggggggactctgccgcaccc cttgcagcgcctgagggtcccgcccccgcctcacgggcc cgtcgagcccgtagcgtggcctccagcttgcgggacaaca accccaggtggactggaaggactggaagatcggcttcca gctgtgcaaccagaacaaatcggactgcttctaccagaca tactcatcagggtggatgcggtgagggagtggtaccgct tccactacatcaacatcctgtcgaggctgccagagactct gccatccctggaggaggacacgctgggcaacttcatcttc gcctgccgcttcaaccaggtctcctgcaaccaggcgaatt actctcacttccaccacccgatgtatggaaactgctatac tttcaatgacaagaacaactccaacctctggatgtcttcc atgcctggaatcaacaacggtctgtccctgatgctgcgcg cagagcagaatgacttcattccctgctgtccacagtgac tggggcccgggtaatggtgcacgggcaggatgaacctgcc tttatggatgatggtggctttaacttgcggcctggcgtgg agacctccatcagcatgaggaaggaaaccctggacagact tggggggcgattatggcgactgcaccaagaatggcagtgat gttcctgttgagaaccttaccctcaaagtacacacagc aggtgtgtattcactcctgcttccaggagagcatgatcaa ggagtgtggctgtgcctacatcttctatccgcggcccccag aacgtggagtactgtgactacagaaagcacagttcctggg ggtactgctactataagctccaggttgacttctcctcaga ccacctgggctgtttcaccaagtgccggaagccatgcagc gtgaccagctaccagctctctgctggttactcacgatggc cctcggtgacatcccaggaatgggtcttccagatgctatc gcgacagaacaattacaccgtcaacaacaagagaaatgga gtggccaaagtcaacatcttcttcaaggagctgaactaca aaaccaattctgagtctccctctgtcacgatggtcaccct cctgtccaacctgggcagccagtggagcctgtggttcggc tcctcggtgttgtctgtggtggagatggctgagctcgtct ttgacctgctggtcatcatgttcctcatgctgctccgaag gttccgaagccgatactggtctccaggccgaggggcagg ggtgctcaggaggtagcctccaccctggcatcctcccctc cttcccacttctgcccccaccccatgtctctgtccttgtc ccagccaggccctgctccctctccagccttgacagcccct cccccctgcctatgccaccctgggccccgcccatctccag
```

-continued ggggctctgcaggggccagttcctccacctgtcctctggg ggggccctga

Length 1923 nucleotides
DNA
Human hENaC beta clone #5 coding sequence
SEQ ID NO: 2 atgcacgtgaagaagtacctGctgaagggcctgcatcggc tgcagaagggccccggctacacgtacaaggagctgctggt gtggtactgcgacaacaccaacacccacggccccaagcgc atcatctgtgagggcccaagaagaaagccatgtggttcc tgctcaccctgctcttcgccgccctcgtctgctggcagtg gggcatcttcatcaggacctacttgagctgggaggtcagc gtctccctctccgtaggcttcaagaccatggacttccccg ccgtcaccatctgcaatgctagccccttcaagtattccaa aatcaagcatttgctgaaggacctggatgagctgatggaa gctgtcctggagagaatcctggctcctgagctaagccatg ccaatgccaccaggaacctgaacttctccatctggaacca cacacccctggtccttattgatgaacggaaccccaccac cccatggtccttgatctctttggagacaaccacaatggct taacaagcagctcagcatcagaaaagatctgtaatgccca cgggtgcaaaatggccatgagactatgtagcctcaacagg acccagtgtaccttccggaacttcaccagtgctacccagg cattgacagagtggtacatcctgcaggccaccaacatctt tgcacaggtgccacagcaggagctagtagagatgagctac cccggcgagcagatgatcctggcctgcctattcggagctg agccctgcaactaccggaacttcacgtccatcttctaccc tcactatggcaactgttacatcttcaactggggcatgaca gagaaggcacttccttcggccaaccctggaactgaattcg gcctgaagttgatcctggacataggccaggaagactacgt ccccttccttgcgtccacggccggggtcaggctgatgctt cacgagcagaggtcataccccticatcagagatgagggca tctacGccatgtcggggacagagacgtccatcggggtact cgtggacaagcttcagcgcatgggggagcctacagcccg tgcaccgtgaatggttctgaggtccccgtccaaaacttct acagtgactacaacacgacctactccatccaggcctgtct tcgctcctgcttccaagaccacatgatccgtaactgcaac tgtggccactacctgtacccactGccccgtggggagaaat actgcaacaaccgggacttcccagactgggcccattgcta ctcagatctacagatgagcgtggcgcagagagagacctgc attggcatgtgcaaggagtcctgcaatgacacccagtaca agatgaccatctccatggctgactggccttctgaggcctc cgaggactggatttccacgtcttgtctcaggagcgggac caaagcaccaatatcaccctgagcaggaagggaattgtca -continued agctcaacatctActtccaagaatttaactatcgcaccat tgaagaatcagcagccaataacatcgtctggctgctctcg aatctgggtggccagtttggcttctggatgggggctctg tgctgtgcctcatcgagtttgggagatcatcatcgactt tgtgtggatcaccatcatcaagctggtggccttggccaag agcctacgcagcggcgagcccaagccagCtacgctggcc caccgccaccgtggccgagctggtggaggcccacaccaa ctttggcttccagcctgacacggccccccgcagcccaac actgggccctaccccagtgagcaggccctgcccatcccag gcacccgccccccaactatgactccctgcgtctgcagcc gctggacgtcatcgagtctgacagtgagggtgatgccatc taa Length 1950 nucleotides
DNA
Human hENaC gamma clone #3 coding sequence
SEQ ID NO: 3 atggcacccggagagaagatcaaagccaaaatcaagaaga atctgcccgtgacgggccctcaggcgccgaccattaaaga gctgatgcggtggtactgcctcaacaccaacacccatggc tgtcgccgcatcgtggtgtcccgcggccgtctgcgccgcc tcctctggatcgggttcacactgactgccgtggccctcat cctctggcagtgcgccctcctcgtcttctccttctatact gtctcagtttccatcaaagtccacttccggaagctggatt ttcctgcagtcaccatctgcaacatcaaccctacaagta cagcaccgttcgccaccttctagctgacttggaacaggag accagagaggccctgaagtccctgtatggctttccagagt cccggaagcgccgagaggcggagtcctggaactccgtctc agagggaaagcagcctagattctcccaccggattccgctg ctgatctttgatcaggatgagaagggcaaggccagggact tcttcacagggAggaagcggaaagtcggcggtagcatcat tcacaaggcttcaaatgtcatgcacatcgagtccaagcaa gtggtgggattccaactgtgctcaaatgacacctccgact gtgccacctacaccttcagctcgggaatcaatgccattca ggagtggtataagctacactacatgaacatcatggcacag gtgcctctggagaagaaatcaacatgagctattctgctg aggagctgctggtgacctgcttctttgatggagtgtcctg tgatgccaggaatttcacgcttttCcaccacccgatgcat gggaattgctatactttcaacaacagagaaaatgagacca ttctcagcacctccatgggggcagcgaatatgggctgca agtcattttgtacataaacgaagaggaatacaacccattc ctcgtgtcctccactggagctaaggtgatcatccatcggc aggatgagtatcccttcgtcgaagatgtgggaacagagat -continued

```
tgagacagcaatggtcacctctataggaatgcacctgaca gagtccttcaagctgagtgagccctacagtcagtgcacgg aggacgggagtgacgtgccaatcaggaacatctacaacgc tgcctactcgctccagatctgccttcattcatgcttccag acaaagatggtggagaaatgtgggtgtgcccagtacagcc agcctctacctcctgcagccaactactgcaactaccagca gcaccccaactggatgtattgttactaccaactgcatcga gcctttgtccaggaagagctgggctgccagtctgtgtgca aggaagcctgcagctttaaagagtggacactaaccacaag cctggcacaatggccatctgtggtttcggagaagtggttg ctgcctgttctcacttgggaccaaggccggcaagtaaaca aaaagctcaacaagacagacttgGccaaaactcttgatatt ctacaaagacctgaaccagagatccatcatggagagccca gccaacagtattgagatgcttctgtccaacttcggtggcc agctgggcctgtggatgagctgctctgttgtctgcgtcat cgagatcatcgaggtcttcttcattgacttcttctctatc attgcccgcgccagtggcagaaagccaaggagtggtggg cctggaaacaggctcccccatgtccagaagctcccgtag cccacagggccaggacaatccagccctggatatagacgat gacctacccactttcaactctgctttgcacctgcctccaG ccctaggaacccaagtgcccggcacaccgcccccaaata caataccttgcgcttggagagggccttttccaaccagctc acagatacccagatgctAgatgagctctga
```

Length 669 amino acids
PRT
Human hENaC alpha clone #3-1-1 amino acid sequence
SEQ ID NO: 4

MEGNKLEEQDSSPPQSTPGLMKGNKREEQGLGPEPAAPQQPTAEEEALIE

FHRSYRELFEFFCNNTTIHGAIRLVCSQHNRMKTAFWAVLWLCTFGMMYW

QFGLLFGEYFSYPVSLNINLNSDKLVFPAVTICTLNPYRYPEIKEELEEL

DRITEQTLFDLYKYSSFTTLVAGSRSRRDLRGTLPHPLQRLRVPPPPHGA

RRARSVASSLRDNNPQVDWKDWKIGFQLCNQNKSDCFYQTYSSGVDAVRE

WYRFHYINILSRLPETLPSLEEDTLGNFIFACRFNQVSCNQANYSHFHHP

MYGNCYTFNDKNNSNLWMSSMPGINNGLSLMLRAEQNDFIPLLSTVTGAR

VMVHGQDEPAFMDDGGFNLRIDGVETSISMRKETLDRLGGDYGDCTKNGS

DVPVENLYPSKYTQQVCIHSCFQESMIKECGCAYIFYPRPQNVEYCDYRK

HSSWGYCYYKLQVDFSSDHLGCFTKCRKPCSVTSYQLSAGYSRWPSVTSQ

EWVFQMLSRQNNYTVNNKRNGVAKVNIFFKELNYKTNSESPSVTMVTLLS

NLGSQWSLWFGSSVLSVVEMAELVFDLLVIMFLMLLRRFRSRYWSPGRGG

RGAQEVASTLASSPPSHFCPHPMSLSLSQPGPAPSPALTAPPPAYATLGP

RPSPGGSAGASSSTCPLGGP

Length 640 amino acids
PRT
Human hENaC beta clone #5 amino acid sequence
SEQ ID NO: 5

MHVKKYLLKGLHRLQKGPGYTYKELLVWYCDNTNTHGPKRIICEGPKKKA

MWFLLTLLFAALVCWQWGIFIRTYLSWEVSVSLSVGFKTMDFPAVTICNA

SPFKYSKIKHLLKDLDELMEAVLERILAPELSHANATRNLNFSIWNHTPL

VLIDERNPHHPMVLDLFGDNHNGLTSSSASEKICNAHGCKMAMRLCSLNR

TQCTFRNFTSATQALTEWYILQATNIFAQVPQQELVEMSYPGEQMILACL

FGAEPCNYRNFTSIFYPHYGNCYIFNWGMTEKALPSANIDGTEFGLKLIL

DIGQEDYVPFLASTAGVRLMLHEQRSYPFIRDEGIYAMSGTETSIGVLVD

KLQRMGEPYSPCTVNGSEVPVQNFYSDYNTTYSIQACLRSCFQDHMIRNC

NCGHYLYPLPRGEKYCNNRDFPDWAHCYSDLQMSVAQRETCIGMCKESCN

DTQYKMTISMADWIDSEASEDWIFHVLSQERDQSTNITLSRKGIVKLNIY

FQEFNYRTIEESAANNIVWLLSNLGGQFGFWMGGSVLCLIEFGEIIIDFV

WITIIKLVALAKSLRQRRAQASYAGPPPTVAELVEAHTNFGFQPDTAPRS

PNTGPYPSEQALPIPGTPPPNYDSLRLQPLDVIESDSEGDAI

Length 650 amino acids
PRT
Human hENaC gamma clone #3 amino acid sequence
SEQ ID NO: 6

MAPGEKIKAKIKKNLIDVTGPQAPTIKELMRWYCLNTNTHGCRRIVVSRG

RLRRLLWIGFTLTAVALILWQCALLVFSFYIVSVSIKVHFRKLDFPAVTI

CNINPYKYSTVRHLLADLEQETREALKSLYGFPESRKRREAESWNSVSEG

KQPRFSHRIPLLIFDQDEKGKARDFFTGRKRKVGGSIIHKASNVMHIESK

QVVGFQLCSNDTSDCATYTFSSGINAIQEWYKLHYMNIMAQVPLEKKINM

SYSAEELLVTCFFDGVSCDARNFTLFHHPMHGNCYTFNNRENETILSTSM

GGSEYGLQVILYINEEEYNPFLVSSTGAKVIIHRQDEYPFVEDVGTEIET

AMVTSIGMHLTESFKLSEPYSQCTEDGSDVPIRNIYNAAYSLQICLHSCF

QTKMVEKCGCAQYSQPLPPAANYCNYQQHPNWMYCYYQLHRAFVQEELGC

QSVCKEACSFKEWTLTTSLAQWPSVVSEKWLLPVLTWDQGRQVNKKLNKT

DLAKLLIFYKDLNQRSIMESPANSIEMLLSNFGGQLGLWMSCSVVCVIEI

IEVFFIDFFSIIARRQWQKAKEWWAWKQAPPCPEAPRSPQGQDNPALDID

DDLPTFNSALHLPPALGTQVPGTPPPKYNTLRLERAFSNQLTDTQMLDEL

Length 1917 nucleotides
DNA
gi|1066456|gb|U38254.1|HSU38254 Human amiloride sensitive sodium channel delta subunit (ΔNaCh) mRNA, complete coding sequence
SEQ ID NO: 7

```
ATGGCTGAGCACCGAAGCATGGACGGGAGAATGGAAGCAGCCACACGGGG

GGGCTCTCACCTCCAGGCTGCAGCCCAGACGCCCCCAGGCCGGGGCCAC

CATCAGCACCACCACCACCACCCAAGGAGGGGCACCAGGAGGGGCTGGTG

GAGCTGCCCGCCTCGTTCCGGGAGCTGCTCACCTTCTTCTGCACCAATGC

CACCATCCACGGCGCCATCCGCCTGGTCTGCTCCCGCGGGAACCGCCTCA

AGACGACGTCCTGGGGCTGCTGTCCCTGGGAGCCCTGGTCGCGCTCTGC

TGGCAGCTGGGGCTCCTCTTTGAGCGTCACTGGCACCGCCCGGTCCTCAT
```

```
GGCCGTCTCTGTGCACTCGGAGCGCAAGCTGCTCCCGCTGGTCACCCTGT

GTGACGGGAACCCACGTCGGCCGAGTCCGGTCCTCCGCCATCTGGAGCTG

CTGGACGAGTTTGCCAGGGAGAACATTGACTCCCTGTACAACGTCAACCT

CAGCAAAGGCAGAGCCGCCCTCTCCGCCACTGTCCCCGCCACGAGCCCC

CCTTCCACCTGGACCGGGAGATCCGTCTGCAGAGGCTGAGCCACTCGGGC

AGCCGGGTCAGAGTGGGGTTCAGACTGTGCAACAGCACGGGCGGCGACTG

CTTTTACCGAGGCTACACGTCAGGCGTGGCGGCTGTCCAGGACTGGTACC

ACTTCCACTATGTGGATATCCTGGCCCTGCTGCCCGCGGCATGGGAGGAC

AGCCACGGGAGCCAGGACGGCCACTTCGTCCTCTCCTGCAGTTACGATGG

CCTGGACTGCCAGGCCCGACAGTTCCGGACCTTCCACCACCCCACCTACG

GCAGCTGCTACACGGTCGATGGCGTCTGGACAGCTCAGCGCCCCGGCATC

ACCCACGGAGTCGGCCTGGTCCTCAGGGTGAGCAGCAGCCTCACCTCCC

TCTGCTGTCCACGCTGGCCGGCATCAGGGTCATGGTTCACGGCCGTAACC

ACACGCCCTTCCTGGGGCACCACAGCTTCAGCGTCCGGCCAGGGACGGAG

GCCACCATCAGCATCCGAGAGGACGAGGTGCACCGGCTCGGGAGCCCCTA

CGGCCACTGCACCGCCGGCGGGGAAGGCGTGGAGGTGGAGCTGCTACACA

ACACCTCCTACACCAGGCAGGCCTGCCTGGTGTCCTGCTTCCAGCAGCTG

ATGGTGGAGACCTGCTCCTGTGGCTACTACCTCCACCCTCTGCCGGCGGG

GGCTGAGTACTGCAGCTCTGCCCGGCACCCTGCCTGGGGACACTGCTTCT

ACCGCCTCTACCAGGACCTGGAGACCCACCGGCTCCCCTGTACCTCCCGC

TGCCCCAGGCCCTGCAGGGAGTCTGCATTCAAGCTCTCCACTGGGACCTC

CAGGTGGCCTTCCGCCAAGTCAGCTGGATGGACTCTGGCCACGCTAGGTG

AACAGGGGCTGCCGCATCAGAGCCACAGACAGAGGAGCAGCCTGGCCAAA

ATCAACATCGTCTACCAGGAGCTCAACTACCGCTCAGTGGAGGAGGCGCC

CGTGTACTCGGTGCCGCAGCTGCTCTCCGCCATGGGCAGCCTCTACAGCC

TGTGGTTTGGGGCCTCCGTCCTCTCCCTCCTGGAGCTCCTGGAGCTGCTG

CTCGATGCTTCTGCCCTCACCCTGGTGCTAGGCGGCCGCCGGCTCCGCAG

GGCGTGGTTCTCCTGGCCCAGAGCCAGCCCTGCCTCAGGGCGTCCAGCT
```
```
CAAGCCAGAGGCCAGTCAGATGCCCCCGCCTGCAGGCGGCACGTCAGATG

ACCCGGAGCCCAGCGGGCCTCATCTCCCACGGGTGATGCTTCCAGGGGTT

CTGGCGGGAGTCTCAGCCGAAGAGAGCTGGGCTGGGCCCCAGCCCCTTGA

GACTCTGGACACCTGA

Length 638 nucleotides
PRT
gi|1710872|sp|P51172|SCAD_HUMAN Amiloride-
sensitive sodium channel delta-subunit amino acid
sequence (Epithelial Na+ channel delta subunit)
(Delta ENaC) (Nonvoltage-gated sodium channel 1
delta subunit) (SCNED) (Delta NaCh)
                                        SEQ ID NO: 8
MAEHRSMDGRMEAATRGGSHLQAAAQTPPRPGPPSAPPPPPKEGHQEGLV

ELPASFRELLTFFCTNATIHGAIRLVCSRGNRLKTTSWGLLSLGALVALC

WQLGLLFERHWHRPVLMAVSVHSERKLLPLVTLCDGNPRRPSPVLRHLEL

LDEFARENIDSLYNVNLSKGRAALSATVPRHEPPFHLDREIRLQRLSHSG

SRVRVGFRLCNSTGGDCFYRGYTSGVAAVQDWYHFHYVDILALLPAAWED

SHGSQDGHFVLSCSYDGLDCQARQFRTFHHPTYGSCYTVDGVWTAQRPGI

THGVGLVLRVEQQPHLPLLSTLAGIRVMVHGRNHTPFLGHHSFSVRPGTE

ATISIREDEVHRLGSPYGHCTAGGEGVEVELLHNTSYTRQACLVSCFQQL

MVETCSCGYYLHPLPAGAEYCSSARHPAWGHCFYRLYQDLETHRLPCTSR

CPRPCRESAFKLSTGTSRWPSAKSAGWTLATLGEQGLPHQSHRQRSSLAK

INIVYQELNYRSVEEAPVYSVPQLLSAMGSLYSLWFGASVLSLLELLELL

LDASALTLVLGGRRLRRAWFSWPRASPASGASSIKPEASQMPPPAGGTSD

DPEPSGPHLPRVMLPGVLAGVSAEESWAGPQPLETLDT
```

While the invention has been described by way of examples and preferred embodiments, it is understood that the words which have been used herein are words of description, rather than words of limitation. Changes may be made, within the purview of the appended claims, without departing from the scope and spirit of the invention in its broader aspects. Although the invention has been described herein with reference to particular means, materials, and embodiments, it is understood that the invention is not limited to the particulars disclosed. The invention extends to all equivalent structures, means, and uses which are within the scope of the appended claims.

What is claimed:

1. A method of identifying a compound which modulates taste by:
   (i) contacting a recombinant or isolated mammalian cell or cell population that expresses a functional human Epithelial Sodium Channel (hENaC) comprising a delta subunit which is at least 95% identical to the polypeptide encoded by SEQ ID NO:7 and an alpha and beta subunit which are respectively at least 95% identical to the polypeptides encoded by SEQ ID NO:1 and 2 with at least one compound,
   (ii) identifying whether the compound modulates the activity of said functional hENaC; and
   (iii) based on whether the compound modulates activity of said hENaC identifying the compound as one potentially modulating taste.

2. The method of claim 1 which includes testing the identified compound in a taste test.

3. The method of claim 1 wherein the isolated cell or cell population is human.

4. The method of claim 1 wherein the isolated cell or cell population is selected from the group consisting of MDCK, BHK, COS, NIH3T3, Swiss3T3 and CHO cells.

5. The method of claim 1 wherein the isolated cell or cell population transiently expresses the alpha (or delta), beta and gamma hENaC subunits.

6. The method of claim 1 wherein the isolated cell or cell population stably expresses the alpha (or delta), beta and gamma hENaC subunits.

7. The method of claim 1 wherein the isolated cell or cell population are comprised in a multi-well test plate device.

8. The method of claim 1 wherein the isolated cell or cell population are loaded with a membrane potential dye.

9. The method of claim 1 wherein the isolated cell or cell population is grown to about 80% confluence.

10. The method of claim 8 wherein the membrane potential dye is CC2-DMPVE , DiSBAC2(3) or ESS-CY4.

11. The method of claim 1 wherein the expressed delta subunit is encoded by the sequence in SEQ ID NO:7.

12. The method of claim 11 wherein the expressed alpha and beta subunits respectively contain the polypeptides encoded by SEQ ID NO:1 and 2.

* * * * *

SEQUENCE LISTING

```
<160> NUMBER OF SEQ ID NOS: 14

<210> SEQ ID NO 1
<211> LENGTH: 2010
<212> TYPE: DNA
<213> ORGANISM: Homo sapiens

<400> SEQUENCE: 1
atggagggga acaagctgga ggagcaggac tctagccctc cacagtccac tccagggctc       60
atgaagggga acaagcgtga ggagcagggg ctgggccccg aacctgcggc gccccagcag      120
cccacggcgg aggaggaggc cctgatcgag ttccaccgct cctaccgaga gctcttcgag      180
ttcttctgca acaacaccac catccacggc gccatccgcc tggtgtgctc ccagcacaac      240
cgcatgaaga cggccttctg ggcagtgctg tggctctgca cctttggcat gatgtactgg      300
```

-continued

| | |
|---|---|
| caattcggcc tgcttttcgg agagtacttc agctaccccg tcagcctcaa catcaacctc | 360 |
| aactcggaca agctcgtctt ccccgcagtg accatctgca ccctcaatcc ctacaggtac | 420 |
| ccggaaatta agaggagct ggaggagctg accgcatca cagagcagac gctctttgac | 480 |
| ctgtacaaat acagctcctt caccactctc gtggccggct cccgcagccg tcgcgacctg | 540 |
| cgggggactc tgccgcaccc cttgcagcgc ctgagggtcc cgcccccgcc tcacggggcc | 600 |
| cgtcgagccc gtagcgtggc ctccagcttg cgggacaaca accccaggt ggactggaag | 660 |
| gactggaaga tcggcttcca gctgtgcaac cagaacaaat cggactgctt ctaccagaca | 720 |
| tactcatcag gggtggatgc ggtgaggag tggtaccgct ccactacat caacatcctg | 780 |
| tcgaggctgc cagagactct gccatccctg aggaggaca cgctgggcaa cttcatcttc | 840 |
| gcctgccgct caaccaggt ctcctgcaac caggcgaatt actctcactt ccaccacccg | 900 |
| atgtatggaa actgctatac tttcaatgac aagaacaact ccaacctctg gatgtcttcc | 960 |
| atgcctggaa tcaacaacgg tctgtccctg atgctgcgcg cagagcagaa tgacttcatt | 1020 |
| cccctgctgt ccacagtgac tggggcccgg gtaatggtgc acgggcagga tgaacctgcc | 1080 |
| tttatggatg atggtggctt taacttgcgg cctggcgtgg agacctccat cagcatgagg | 1140 |
| aaggaaaccc tggacagact tgggggcgat tatgcgact gcaccaagaa tggcagtgat | 1200 |
| gttcctgttg agaaccttta cccttcaaag tacacacagc aggtgtgtat tcactcctgc | 1260 |
| ttccaggaga gcatgatcaa ggagtgtggc tgtgcctaca tcttctatcc gcggccccag | 1320 |
| aacgtggagt actgtgacta cagaaagcac agttcctggg ggtactgcta ctataagctc | 1380 |
| caggttgact tctcctcaga ccacctgggc tgtttcacca agtccggaa gccatgcagc | 1440 |
| gtgaccagct accagctctc tgctggttac tcacgatggc cctcggtgac atcccaggaa | 1500 |
| tgggtcttcc agatgctatc gcgacagaac aattacaccg tcaacaacaa gagaaatgga | 1560 |
| gtggccaaag tcaacatctt cttcaaggag ctgaactaca aaaccaattc tgagtctccc | 1620 |
| tctgtcacga tggtcaccct cctgtccaac ctgggcagcc agtggagcct gtggttcggc | 1680 |
| tcctcggtgt tgtctgtggt ggagatggct gagctcgtct ttgacctgct ggtcatcatg | 1740 |
| ttcctcatgc tgctccgaag gttccgaagc cgatactggt ctccaggccg aggggggcagg | 1800 |
| ggtgctcagg aggtagcctc caccctggca tcctcccctc cttcccactt ctgccccac | 1860 |
| cccatgtctc tgtccttgtc ccagccaggc cctgctccct ctccagcctt gacagccct | 1920 |
| cccctgcct atgccaccct gggccccgc ccatctccag ggggctctgc aggggccagt | 1980 |
| tcctccacct gtcctctggg ggggccctga | 2010 |

<210> SEQ ID NO 2
<211> LENGTH: 1923
<212> TYPE: DNA
<213> ORGANISM: Homo sapiens

<400> SEQUENCE: 2

| | |
|---|---|
| atgcacgtga agaagtacct gctgaagggc ctgcatcggc tgcagaaggg ccccggctac | 60 |
| acgtacaagg agctgctggt gtggtactgc gacaacacca acacccacgg ccccaagcgc | 120 |
| atcatctgtg aggggcccaa gaagaaagcc atgtggttcc tgctcaccct gctcttcgcc | 180 |
| gccctcgtct gctggcagtg gggcatcttc atcaggacct acttgagctg ggaggtcagc | 240 |
| gtctccctct ccgtaggctt caagaccatg gacttccccg ccgtcaccat ctgcaatgct | 300 |
| agccccttca gtattccaa aatcaagcat ttgctgaagg acctggatga gctgatggaa | 360 |

-continued

| | |
|---|---|
| gctgtcctgg agagaatcct ggctcctgag ctaagccatg ccaatgccac caggaacctg | 420 |
| aacttctcca tctggaacca cacaccctg gtccttattg atgaacggaa ccccaccac | 480 |
| cccatggtcc ttgatctctt tggagacaac acaatggct taacaagcag ctcagcatca | 540 |
| gaaaagatct gtaatgccca cgggtgcaaa atggccatga actatgtag cctcaacagg | 600 |
| acccagtgta ccttccggaa cttcaccagt gctacccagg cattgacaga gtggtacatc | 660 |
| ctgcaggcca ccaacatctt tgcacaggtg ccacagcagg agctagtaga gatgagctac | 720 |
| cccggcgagc agatgatcct ggcctgccta ttcggagctg agccctgcaa ctaccggaac | 780 |
| ttcacgtcca tcttctaccc tcactatggc aactgttaca tcttcaactg ggcatgaca | 840 |
| gagaaggcac ttccttcggc caaccctgga actgaattcg gcctgaagtt gatcctggac | 900 |
| ataggccagg aagactacgt ccccttcctt gcgtccacgg ccggggtcag gctgatgctt | 960 |
| cacgagcaga ggtcataccc cttcatcaga gatgagggca tctacgccat gtcggggaca | 1020 |
| gagacgtcca tcgggtact cgtggacaag cttcagcgca tgggggagcc ctacagcccg | 1080 |
| tgcaccgtga atggttctga ggtccccgtc caaaacttct acagtgacta caacacgacc | 1140 |
| tactccatcc aggcctgtct tcgctcctgc ttccaagacc acatgatccg taactgcaac | 1200 |
| tgtggccact acctgtaccc actgccccgt ggggagaaat actgcaacaa ccgggacttc | 1260 |
| ccagactggg cccattgcta ctcagatcta cagatgagcg tggcgcagag agagacctgc | 1320 |
| attggcatgt gcaaggagtc ctgcaatgac acccagtaca agatgaccat ctccatggct | 1380 |
| gactggcctt ctgaggcctc cgaggactgg attttccacg tcttgtctca ggagcgggac | 1440 |
| caaagcacca atatcaccct gagcaggaag ggaattgtca agctcaacat ctacttccaa | 1500 |
| gaatttaact atcgcaccat tgaagaatca gcagccaata acatcgtctg ctgctctcg | 1560 |
| aatctgggtg ccagtttgg cttctggatg ggggctctg tgctgtgcct catcgagttt | 1620 |
| ggggagatca tcatcgactt tgtgtggatc accatcatca agctggtggc cttggccaag | 1680 |
| agcctacggc agcggcgagc ccaagccagc tacgctggcc caccgcccac cgtgccgag | 1740 |
| ctggtggagg cccacaccaa cttggcttc cagcctgaca cggcccccg cagccccaac | 1800 |
| actgggccct accccagtga gcaggccctg cccatcccag caccccgcc cccaactat | 1860 |
| gactccctgc gtctgcagcc gctggacgtc atcgagtctg acagtgaggg tgatgccatc | 1920 |
| taa | 1923 |

<210> SEQ ID NO 3
<211> LENGTH: 1950
<212> TYPE: DNA
<213> ORGANISM: Homo sapiens

<400> SEQUENCE: 3

| | |
|---|---|
| atggcacccg gagagaagat caaagccaaa atcaagaaga atctgcccgt gacgggccct | 60 |
| caggcgccga ccattaaaga gctgatgcgg tggtactgcc tcaacaccaa cacccatggc | 120 |
| tgtcgccgca tcgtggtgtc ccgcggccgt ctgcgccgcc tcctctggat cgggttcaca | 180 |
| ctgactgccg tggccctcat cctctggcag tgcgccctcc tcgtcttctc cttctatact | 240 |
| gtctcagttt ccatcaaagt ccacttccgg aagctggatt tccctgcagt caccatctgc | 300 |
| aacatcaacc cctacaagta cagcaccgtt cgccaccttc tagctgactt ggaacaggag | 360 |
| accagagagg ccctgaagtc cctgtatggc tttccagagt cccggaagcg ccgagaggcg | 420 |
| gagtcctgga actccgtctc agagggaaag cagcctagat tctcccaccg gattccgctg | 480 |
| ctgatctttg atcaggatga agggcaag gccagggact tcttcacagg gaggaagcgg | 540 |

```
aaagtcggcg gtagcatcat tcacaaggct tcaaatgtca tgcacatcga gtccaagcaa    600
gtggtgggat tccaactgtg ctcaaatgac acctccgact gtgccaccta caccttcagc    660
tcgggaatca atgccattca ggagtggtat aagctacact acatgaacat catggcacag    720
gtgcctctgg agaagaaaat caacatgagc tattctgctg aggagctgct ggtgacctgc    780
ttctttgatg gagtgtcctg tgatgccagg aatttcacgc ttttccacca cccgatgcat    840
gggaattgct atactttcaa caacagagaa atgagacca ttctcagcac tccatgggg     900
ggcagcgaat atgggctgca agtcattttg tacataaacg aagaggaata caacccattc    960
ctcgtgtcct ccactggagc taaggtgatc atccatcggc aggatgagta tcccttcgtc   1020
gaagatgtgg gaacagagat tgagacagca atggtcacct ctataggaat gcacctgaca   1080
gagtccttca gctgagtga gccctacagt cagtgcacgg aggacgggag tgacgtgcca   1140
atcaggaaca tctacaacgc tgcctactcg ctccagatct gccttcattc atgcttccag   1200
acaaagatgg tggagaaatg tgggtgtgcc cagtacagcc agcctctacc tcctgcagcc   1260
aactactgca actaccagca gcaccccaac tggatgtatt gttactacca actgcatcga   1320
gcctttgtcc aggaagagct gggctgccag tctgtgtgca aggaagcctg cagctttaaa   1380
gagtggacac taaccacaag cctggcacaa tggccatctg tggtttcgga agtggttg    1440
ctgcctgttc tcacttggga ccaaggccgg caagtaaaca aaaagctcaa caagacagac   1500
ttggccaaac tcttgatatt ctacaaagac ctgaaccaga gatccatcat ggagagccca   1560
gccaacagta ttgagatgct tctgtccaac ttcggtggcc agctgggcct gtggatgagc   1620
tgctctgttg tctgcgtcat cgagatcatc gaggtcttct tcattgactt cttctctatc   1680
attgcccgcc gccagtggca gaaagccaag gagtggtggg cctggaaaca ggctcccca   1740
tgtccagaag ctccccgtag cccacagggc caggacaatc cagccctgga tatagacgat   1800
gacctaccca ctttcaactc tgctttgcac ctgcctccag ccctaggaac ccaagtgccc   1860
ggcacaccgc ccccaaata caataccttg cgcttggaga gggccttttc caaccagctc   1920
acagataccc agatgctaga tgagctctga                                     1950
```

<210> SEQ ID NO 4
<211> LENGTH: 669
<212> TYPE: PRT
<213> ORGANISM: Homo sapiens

<400> SEQUENCE: 4

Met Glu Gly Asn Lys Leu Glu Glu Gln Asp Ser Ser Pro Pro Gln Ser
1               5                   10                  15

Thr Pro Gly Leu Met Lys Gly Asn Lys Arg Glu Glu Gln Gly Leu Gly
            20                  25                  30

Pro Glu Pro Ala Ala Pro Gln Gln Pro Thr Ala Glu Glu Ala Leu
        35                  40                  45

Ile Glu Phe His Arg Ser Tyr Arg Glu Leu Phe Glu Phe Phe Cys Asn
    50                  55                  60

Asn Thr Thr Ile His Gly Ala Ile Arg Leu Val Cys Ser Gln His Asn
65                  70                  75                  80

Arg Met Lys Thr Ala Phe Trp Ala Val Leu Trp Leu Cys Thr Phe Gly
                85                  90                  95

Met Met Tyr Trp Gln Phe Gly Leu Leu Phe Gly Glu Tyr Phe Ser Tyr
            100                 105                 110

Pro Val Ser Leu Asn Ile Asn Leu Asn Ser Asp Lys Leu Val Phe Pro

-continued

```
            115                 120                 125
Ala Val Thr Ile Cys Thr Leu Asn Pro Tyr Arg Tyr Pro Glu Ile Lys
        130                 135                 140

Glu Glu Leu Glu Glu Leu Asp Arg Ile Thr Glu Gln Thr Leu Phe Asp
145                 150                 155                 160

Leu Tyr Lys Tyr Ser Ser Phe Thr Thr Leu Val Ala Gly Ser Arg Ser
                165                 170                 175

Arg Arg Asp Leu Arg Gly Thr Leu Pro His Pro Leu Gln Arg Leu Arg
            180                 185                 190

Val Pro Pro Pro His Gly Ala Arg Arg Ala Arg Ser Val Ala Ser
        195                 200                 205

Ser Leu Arg Asp Asn Asn Pro Gln Val Asp Trp Lys Asp Trp Lys Ile
        210                 215                 220

Gly Phe Gln Leu Cys Asn Gln Asn Lys Ser Asp Cys Phe Tyr Gln Thr
225                 230                 235                 240

Tyr Ser Ser Gly Val Asp Ala Val Arg Glu Trp Tyr Arg Phe His Tyr
                245                 250                 255

Ile Asn Ile Leu Ser Arg Leu Pro Glu Thr Leu Pro Ser Leu Glu Glu
            260                 265                 270

Asp Thr Leu Gly Asn Phe Ile Phe Ala Cys Arg Phe Asn Gln Val Ser
        275                 280                 285

Cys Asn Gln Ala Asn Tyr Ser His Phe His His Pro Met Tyr Gly Asn
290                 295                 300

Cys Tyr Thr Phe Asn Asp Lys Asn Asn Ser Asn Leu Trp Met Ser Ser
305                 310                 315                 320

Met Pro Gly Ile Asn Asn Gly Leu Ser Leu Met Leu Arg Ala Glu Gln
                325                 330                 335

Asn Asp Phe Ile Pro Leu Leu Ser Thr Val Thr Gly Ala Arg Val Met
            340                 345                 350

Val His Gly Gln Asp Glu Pro Ala Phe Met Asp Asp Gly Gly Phe Asn
        355                 360                 365

Leu Arg Pro Gly Val Glu Thr Ser Ile Ser Met Arg Lys Glu Thr Leu
        370                 375                 380

Asp Arg Leu Gly Gly Asp Tyr Gly Asp Cys Thr Lys Asn Gly Ser Asp
385                 390                 395                 400

Val Pro Val Glu Asn Leu Tyr Pro Ser Lys Tyr Thr Gln Gln Val Cys
                405                 410                 415

Ile His Ser Cys Phe Gln Glu Ser Met Ile Lys Glu Cys Gly Cys Ala
            420                 425                 430

Tyr Ile Phe Tyr Pro Arg Pro Gln Asn Val Glu Tyr Cys Asp Tyr Arg
        435                 440                 445

Lys His Ser Ser Trp Gly Tyr Cys Tyr Tyr Lys Leu Gln Val Asp Phe
        450                 455                 460

Ser Ser Asp His Leu Gly Cys Phe Thr Lys Cys Arg Lys Pro Cys Ser
465                 470                 475                 480

Val Thr Ser Tyr Gln Leu Ser Ala Gly Tyr Ser Arg Trp Pro Ser Val
                485                 490                 495

Thr Ser Gln Glu Trp Val Phe Gln Met Leu Ser Arg Gln Asn Asn Tyr
            500                 505                 510

Thr Val Asn Asn Lys Arg Asn Gly Val Ala Lys Val Asn Ile Phe Phe
        515                 520                 525

Lys Glu Leu Asn Tyr Lys Thr Asn Ser Glu Ser Pro Ser Val Thr Met
        530                 535                 540
```

```
Val Thr Leu Leu Ser Asn Leu Gly Ser Gln Trp Ser Leu Trp Phe Gly
545                 550                 555                 560

Ser Ser Val Leu Ser Val Val Glu Met Ala Glu Leu Val Phe Asp Leu
                565                 570                 575

Leu Val Ile Met Phe Leu Met Leu Leu Arg Arg Phe Arg Ser Arg Tyr
            580                 585                 590

Trp Ser Pro Gly Arg Gly Arg Gly Ala Gln Glu Val Ala Ser Thr
        595                 600                 605

Leu Ala Ser Ser Pro Pro Ser His Phe Cys Pro His Pro Met Ser Leu
    610                 615                 620

Ser Leu Ser Gln Pro Gly Pro Ala Pro Ser Pro Ala Leu Thr Ala Pro
625                 630                 635                 640

Pro Pro Ala Tyr Ala Thr Leu Gly Pro Arg Pro Ser Pro Gly Gly Ser
            645                 650                 655

Ala Gly Ala Ser Ser Ser Thr Cys Pro Leu Gly Gly Pro
            660                 665

<210> SEQ ID NO 5
<211> LENGTH: 640
<212> TYPE: PRT
<213> ORGANISM: Homo sapiens

<400> SEQUENCE: 5

Met His Val Lys Lys Tyr Leu Leu Lys Gly Leu His Arg Leu Gln Lys
1               5                   10                  15

Gly Pro Gly Tyr Thr Tyr Lys Glu Leu Leu Val Trp Tyr Cys Asp Asn
            20                  25                  30

Thr Asn Thr His Gly Pro Lys Arg Ile Ile Cys Glu Gly Pro Lys Lys
        35                  40                  45

Lys Ala Met Trp Phe Leu Leu Thr Leu Leu Phe Ala Ala Leu Val Cys
50                  55                  60

Trp Gln Trp Gly Ile Phe Ile Arg Thr Tyr Leu Ser Trp Glu Val Ser
65                  70                  75                  80

Val Ser Leu Ser Val Gly Phe Lys Thr Met Asp Phe Pro Ala Val Thr
                85                  90                  95

Ile Cys Asn Ala Ser Pro Phe Lys Tyr Ser Lys Ile Lys His Leu Leu
            100                 105                 110

Lys Asp Leu Asp Glu Leu Met Glu Ala Val Leu Glu Arg Ile Leu Ala
        115                 120                 125

Pro Glu Leu Ser His Ala Asn Ala Thr Arg Asn Leu Asn Phe Ser Ile
130                 135                 140

Trp Asn His Thr Pro Leu Val Leu Ile Asp Glu Arg Asn Pro His His
145                 150                 155                 160

Pro Met Val Leu Asp Leu Phe Gly Asp Asn His Asn Gly Leu Thr Ser
                165                 170                 175

Ser Ser Ala Ser Glu Lys Ile Cys Asn Ala His Gly Cys Lys Met Ala
            180                 185                 190

Met Arg Leu Cys Ser Leu Asn Arg Thr Gln Cys Thr Phe Arg Asn Phe
        195                 200                 205

Thr Ser Ala Thr Gln Ala Thr Glu Trp Tyr Ile Leu Gln Ala Thr
210                 215                 220

Asn Ile Phe Ala Gln Val Pro Gln Gln Glu Leu Val Glu Met Ser Tyr
225                 230                 235                 240

Pro Gly Glu Gln Met Ile Leu Ala Cys Leu Phe Gly Ala Glu Pro Cys
```

```
                    245                 250                 255
Asn Tyr Arg Asn Phe Thr Ser Ile Phe Tyr Pro His Tyr Gly Asn Cys
                260                 265                 270

Tyr Ile Phe Asn Trp Gly Met Thr Glu Lys Ala Leu Pro Ser Ala Asn
            275                 280                 285

Pro Gly Thr Glu Phe Gly Leu Lys Leu Ile Leu Asp Ile Gly Gln Glu
        290                 295                 300

Asp Tyr Val Pro Phe Leu Ala Ser Thr Ala Gly Val Arg Leu Met Leu
305                 310                 315                 320

His Glu Gln Arg Ser Tyr Pro Phe Ile Arg Asp Glu Gly Ile Tyr Ala
                325                 330                 335

Met Ser Gly Thr Glu Thr Ser Ile Gly Val Leu Val Asp Lys Leu Gln
                340                 345                 350

Arg Met Gly Glu Pro Tyr Ser Pro Cys Thr Val Asn Gly Ser Glu Val
                355                 360                 365

Pro Val Gln Asn Phe Tyr Ser Asp Tyr Asn Thr Thr Tyr Ser Ile Gln
        370                 375                 380

Ala Cys Leu Arg Ser Cys Phe Gln Asp His Met Ile Arg Asn Cys Asn
385                 390                 395                 400

Cys Gly His Tyr Leu Tyr Pro Leu Pro Arg Gly Glu Lys Tyr Cys Asn
                405                 410                 415

Asn Arg Asp Phe Pro Asp Trp Ala His Cys Tyr Ser Asp Leu Gln Met
            420                 425                 430

Ser Val Ala Gln Arg Glu Thr Cys Ile Gly Met Cys Lys Glu Ser Cys
        435                 440                 445

Asn Asp Thr Gln Tyr Lys Met Thr Ile Ser Met Ala Asp Trp Pro Ser
450                 455                 460

Glu Ala Ser Glu Asp Trp Ile Phe His Val Leu Ser Gln Glu Arg Asp
465                 470                 475                 480

Gln Ser Thr Asn Ile Thr Leu Ser Arg Lys Gly Ile Val Lys Leu Asn
                485                 490                 495

Ile Tyr Phe Gln Glu Phe Asn Tyr Arg Thr Ile Glu Glu Ser Ala Ala
                500                 505                 510

Asn Asn Ile Val Trp Leu Leu Ser Asn Leu Gly Gly Gln Phe Gly Phe
            515                 520                 525

Trp Met Gly Gly Ser Val Leu Cys Leu Ile Glu Phe Gly Glu Ile Ile
        530                 535                 540

Ile Asp Phe Val Trp Ile Thr Ile Lys Leu Val Ala Leu Ala Lys
545                 550                 555                 560

Ser Leu Arg Gln Arg Arg Ala Gln Ala Ser Tyr Ala Gly Pro Pro Pro
                565                 570                 575

Thr Val Ala Glu Leu Val Glu Ala His Thr Asn Phe Gly Phe Gln Pro
                580                 585                 590

Asp Thr Ala Pro Arg Ser Pro Asn Thr Gly Pro Tyr Pro Ser Glu Gln
            595                 600                 605

Ala Leu Pro Ile Pro Gly Thr Pro Pro Asn Tyr Asp Ser Leu Arg
        610                 615                 620

Leu Gln Pro Leu Asp Val Ile Glu Ser Asp Ser Glu Gly Asp Ala Ile
625                 630                 635                 640

<210> SEQ ID NO 6
<211> LENGTH: 649
<212> TYPE: PRT
<213> ORGANISM: Homo sapiens
```

```
<400> SEQUENCE: 6

Met Ala Pro Gly Glu Lys Ile Lys Ala Lys Ile Lys Lys Asn Leu Pro
1               5                   10                  15

Val Thr Gly Pro Gln Ala Pro Thr Ile Lys Glu Leu Met Arg Trp Tyr
            20                  25                  30

Cys Leu Asn Thr Asn Thr His Gly Cys Arg Arg Ile Val Val Ser Arg
                35                  40                  45

Gly Arg Leu Arg Arg Leu Leu Trp Ile Gly Phe Thr Leu Thr Ala Val
        50                  55                  60

Ala Leu Ile Leu Trp Gln Cys Ala Leu Leu Val Phe Ser Phe Tyr Thr
65                  70                  75                  80

Val Ser Val Ser Ile Lys Val His Phe Arg Lys Leu Asp Phe Pro Ala
                85                  90                  95

Val Thr Ile Cys Asn Ile Asn Pro Tyr Lys Tyr Ser Thr Val Arg His
                100                 105                 110

Leu Leu Ala Asp Leu Glu Gln Glu Thr Arg Glu Ala Leu Lys Ser Leu
            115                 120                 125

Tyr Gly Phe Pro Glu Ser Arg Lys Arg Glu Ala Glu Ser Trp Asn
        130                 135                 140

Ser Val Ser Glu Gly Lys Gln Pro Arg Phe Ser His Arg Ile Pro Leu
145                 150                 155                 160

Leu Ile Phe Asp Gln Asp Glu Lys Gly Lys Ala Arg Asp Phe Phe Thr
                165                 170                 175

Gly Arg Lys Arg Lys Val Gly Gly Ser Ile Ile His Lys Ala Ser Asn
            180                 185                 190

Val Met His Ile Glu Ser Lys Gln Val Val Gly Phe Gln Leu Cys Ser
        195                 200                 205

Asn Asp Thr Ser Asp Cys Ala Thr Tyr Thr Phe Ser Ser Gly Ile Asn
        210                 215                 220

Ala Ile Gln Glu Trp Tyr Lys Leu His Tyr Met Asn Ile Met Ala Gln
225                 230                 235                 240

Val Pro Leu Glu Lys Lys Ile Asn Met Ser Tyr Ser Ala Glu Glu Leu
                245                 250                 255

Leu Val Thr Cys Phe Phe Asp Gly Val Ser Cys Asp Ala Arg Asn Phe
            260                 265                 270

Thr Leu Phe His His Pro Met His Gly Asn Cys Tyr Thr Phe Asn Asn
        275                 280                 285

Arg Glu Asn Glu Thr Ile Leu Ser Thr Ser Met Gly Gly Ser Glu Tyr
        290                 295                 300

Gly Leu Gln Val Ile Leu Tyr Ile Asn Glu Glu Tyr Asn Pro Phe
305                 310                 315                 320

Leu Val Ser Ser Thr Gly Ala Lys Val Ile Ile His Arg Gln Asp Glu
                325                 330                 335

Tyr Pro Phe Val Glu Asp Val Gly Thr Glu Ile Glu Thr Ala Met Val
            340                 345                 350

Thr Ser Ile Gly Met His Leu Thr Glu Ser Phe Lys Leu Ser Glu Pro
        355                 360                 365

Tyr Ser Gln Cys Thr Glu Asp Gly Ser Asp Val Pro Ile Arg Asn Ile
        370                 375                 380

Tyr Asn Ala Ala Tyr Ser Leu Gln Ile Cys Leu His Ser Cys Phe Gln
385                 390                 395                 400

Thr Lys Met Val Glu Lys Cys Gly Cys Ala Gln Tyr Ser Gln Pro Leu
```

```
            405                 410                 415
Pro Pro Ala Ala Asn Tyr Cys Asn Tyr Gln Gln His Pro Asn Trp Met
            420                 425                 430

Tyr Cys Tyr Tyr Gln Leu His Arg Ala Phe Val Gln Glu Glu Leu Gly
            435                 440                 445

Cys Gln Ser Val Cys Lys Glu Ala Cys Ser Phe Lys Glu Trp Thr Leu
            450                 455                 460

Thr Thr Ser Leu Ala Gln Trp Pro Ser Val Val Ser Glu Lys Trp Leu
465                 470                 475                 480

Leu Pro Val Leu Thr Trp Asp Gln Gly Arg Gln Val Asn Lys Lys Leu
                485                 490                 495

Asn Lys Thr Asp Leu Ala Lys Leu Leu Ile Phe Tyr Lys Asp Leu Asn
            500                 505                 510

Gln Arg Ser Ile Met Glu Ser Pro Ala Asn Ser Ile Glu Met Leu Leu
            515                 520                 525

Ser Asn Phe Gly Gly Gln Leu Gly Leu Trp Met Ser Cys Ser Val Val
            530                 535                 540

Cys Val Ile Glu Ile Ile Glu Val Phe Phe Ile Asp Phe Phe Ser Ile
545                 550                 555                 560

Ile Ala Arg Arg Gln Trp Gln Lys Ala Lys Glu Trp Trp Ala Trp Lys
                565                 570                 575

Gln Ala Pro Pro Cys Pro Glu Ala Pro Arg Ser Pro Gln Gly Gln Asp
            580                 585                 590

Asn Pro Ala Leu Asp Ile Asp Asp Asp Leu Pro Thr Phe Asn Ser Ala
            595                 600                 605

Leu His Leu Pro Pro Ala Leu Gly Thr Gln Val Pro Gly Thr Pro Pro
610                 615                 620

Pro Lys Tyr Asn Thr Leu Arg Leu Glu Arg Ala Phe Ser Asn Gln Leu
625                 630                 635                 640

Thr Asp Thr Gln Met Leu Asp Glu Leu
                645

<210> SEQ ID NO 7
<211> LENGTH: 1916
<212> TYPE: DNA
<213> ORGANISM: Homo sapiens

<400> SEQUENCE: 7
atggctgagc accgaagcat ggacgggaga atggaagcag ccacacgggg gggctctcac      60
ctccaggctg cagcccagac gcccccccagg ccggggccac catcagcacc accaccacca     120
cccaaggagg ggcaccagga ggggctggtg agctgcccg cctcgttccg ggagctgctc       180
accttcttct gcaccaatgc caccatccac ggcgccatcc gcctggtctg ctcccgcggg      240
aaccgcctca gacgacgtc ctgggggctg ctgtccctgg agccctggt cgcgctctgc        300 tggcagctgg ggtcctcttt tgagcgtcac tggcaccgcc cggtcctcat ggccgtctct     360
gtgcactcgg agcgcaagct gctcccgctg gtcaccctgt gtgacgggaa cccacgtcgg     420
ccgagtccgg tcctccgcca tctggagctg ctggacgagt tgccaggga gaacattgac      480 tccctgtaca acgtcaacct cagcaaaggc agagccgccc tctccgccac tgtccccgc     540 cacgagcccc ccttccacct ggaccgggag atccgtctgc agaggctgag ccactcgggc    600
agccgggtca gagtggggtt cagactgtgc aacagcacgg gcggcgactg ctttttaccga    660 ggctacacgt caggcgtggc ggctgtccag gactggtacc acttccacta tgtggatatc     720
```

```
ctggccctgc tgcccgcggc atgggaggac agccacggga gccaggacgg ccacttcgtc    780
ctctcctgca gttacgatgg cctggactgc caggcccgac agttccggac cttccaccac    840
cccacctacg gcagctgcta cacggtcgat ggcgtctgga cagctcagcg ccccggcatc    900
acccacggag tcggcctggt cctcagggtt gagcagcagc ctcacctccc tctgctgtcc    960
acgctggccg gcatcagggt catggttcac ggccgtaacc acacgccctt cctggggcac   1020
cacagcttca gcgtccggcc agggacggag gccaccatca gcatccgaga ggacgaggtg   1080
caccggctcg ggagccccta cggccactgc accgccggcg gggaaggcgt ggaggtggag   1140
ctgctacaca acacctccta caccaggcag gcctgcctgg tgtcctgctt ccagcagctg   1200
atggtggaga cctgctcctg tggctactac ctccaccctc tgccggcggg ggctgagtac   1260
tgcagctctg cccggcaccc tgcctgggga cactgcttct accgcctcta ccaggacctg   1320
gagacccacc ggctcccctg tacctcccgc tgccccaggc cctgcaggga gtctgcattc   1380 aagtctctcca ctgggacctc caggtggcct tccgccaagt cagctggatg gactctggcc   1440
acgctaggtg aacaggggct gccgcatcag agccacagac agaggagcag cctggccaaa   1500
atcaacatcg tctaccagga gctcaactac cgctcagtgg aggaggcgcc cgtgtactcg   1560
gtgccgcagc tgctctccgc catgggcagc ctctacagcc tgtggtttgg ggcctccgtc   1620
ctctccctcc tggagctcct ggagctgctg ctcgatgctt ctgccctcac cctggtgcta   1680
ggcggccgcc ggctccgcag ggcgtggttc tcctggccca gagccagccc tgcctcaggg   1740
gcgtccagct caagccagag gccagtcaga tgccccgcc tgcaggcggc acgtcagatg   1800
acccggagcc cagcgggcct catctcccac gggtgatgct tccaggggtt ctggcgggag   1860
tctcagccga agagagctgg gctgggcccc agcccttga gactctggac acctga         1916

<210> SEQ ID NO 8
<211> LENGTH: 638
<212> TYPE: PRT
<213> ORGANISM: Homo sapiens

<400> SEQUENCE: 8

Met Ala Glu His Arg Ser Met Asp Gly Arg Met Glu Ala Ala Thr Arg
1               5                   10                  15

Gly Gly Ser His Leu Gln Ala Ala Gln Thr Pro Pro Arg Pro Gly
            20                  25                  30

Pro Pro Ser Ala Pro Pro Pro Lys Glu Gly His Gln Glu Gly
        35                  40                  45

Leu Val Glu Leu Pro Ala Ser Phe Arg Glu Leu Thr Phe Phe Cys
    50                  55                  60

Thr Asn Ala Thr Ile His Gly Ala Ile Arg Leu Val Cys Ser Arg Gly
65                  70                  75                  80

Asn Arg Leu Lys Thr Thr Ser Trp Gly Leu Leu Ser Leu Gly Ala Leu
                85                  90                  95

Val Ala Leu Cys Trp Gln Leu Gly Leu Leu Phe Glu Arg His Trp His
            100                 105                 110

Arg Pro Val Leu Met Ala Val Ser Val His Ser Glu Arg Lys Leu Leu
        115                 120                 125

Pro Leu Val Thr Leu Cys Asp Gly Asn Pro Arg Arg Pro Ser Pro Val
    130                 135                 140

Leu Arg His Leu Glu Leu Leu Asp Glu Phe Ala Arg Glu Asn Ile Asp
145                 150                 155                 160

Ser Leu Tyr Asn Val Asn Leu Ser Lys Gly Arg Ala Ala Leu Ser Ala
```

```
            165                 170                 175
Thr Val Pro Arg His Glu Pro Phe His Leu Asp Arg Glu Ile Arg
            180                 185                 190
Leu Gln Arg Leu Ser His Ser Gly Arg Val Arg Val Gly Phe Arg
            195                 200                 205
Leu Cys Asn Ser Thr Gly Gly Asp Cys Phe Tyr Arg Gly Tyr Thr Ser
    210                 215                 220
Gly Val Ala Ala Val Gln Asp Trp Tyr His Phe His Tyr Val Asp Ile
225                 230                 235                 240
Leu Ala Leu Leu Pro Ala Ala Trp Glu Asp Ser His Gly Ser Gln Asp
                245                 250                 255
Gly His Phe Val Leu Ser Cys Ser Tyr Asp Gly Leu Asp Cys Gln Ala
                260                 265                 270
Arg Gln Phe Arg Thr Phe His His Pro Thr Tyr Gly Ser Cys Tyr Thr
            275                 280                 285
Val Asp Gly Val Trp Thr Ala Gln Arg Pro Gly Ile Thr His Gly Val
        290                 295                 300
Gly Leu Val Leu Arg Val Glu Gln Gln Pro His Leu Pro Leu Leu Ser
305                 310                 315                 320
Thr Leu Ala Gly Ile Arg Val Met Val His Gly Arg Asn His Thr Pro
                325                 330                 335
Phe Leu Gly His His Ser Phe Ser Val Arg Pro Gly Thr Glu Ala Thr
                340                 345                 350
Ile Ser Ile Arg Glu Asp Glu Val His Arg Leu Gly Ser Pro Tyr Gly
                355                 360                 365
His Cys Thr Ala Gly Gly Glu Gly Val Glu Val Glu Leu Leu His Asn
        370                 375                 380
Thr Ser Tyr Thr Arg Gln Ala Cys Leu Val Ser Cys Phe Gln Gln Leu
385                 390                 395                 400
Met Val Glu Thr Cys Ser Cys Gly Tyr Tyr Leu His Pro Leu Pro Ala
                405                 410                 415
Gly Ala Glu Tyr Cys Ser Ser Ala Arg His Pro Ala Trp Gly His Cys
                420                 425                 430
Phe Tyr Arg Leu Tyr Gln Asp Leu Glu Thr His Arg Leu Pro Cys Thr
            435                 440                 445
Ser Arg Cys Pro Arg Pro Cys Arg Glu Ser Ala Phe Lys Leu Ser Thr
    450                 455                 460
Gly Thr Ser Arg Trp Pro Ser Ala Lys Ser Ala Gly Trp Thr Leu Ala
465                 470                 475                 480
Thr Leu Gly Glu Gln Gly Leu Pro His Gln Ser His Arg Gln Arg Ser
                485                 490                 495
Ser Leu Ala Lys Ile Asn Ile Val Tyr Gln Glu Leu Asn Tyr Arg Ser
            500                 505                 510
Val Glu Glu Ala Pro Val Tyr Ser Val Pro Gln Leu Leu Ser Ala Met
            515                 520                 525
Gly Ser Leu Tyr Ser Leu Trp Phe Gly Ala Ser Val Leu Ser Leu Leu
            530                 535                 540
Glu Leu Leu Glu Leu Leu Leu Asp Ala Ser Ala Leu Thr Leu Val Leu
545                 550                 555                 560
Gly Gly Arg Arg Leu Arg Arg Ala Trp Phe Ser Trp Pro Arg Ala Ser
                565                 570                 575
Pro Ala Ser Gly Ala Ser Ser Ile Lys Pro Glu Ala Ser Gln Met Pro
            580                 585                 590
```

```
Pro Pro Ala Gly Gly Thr Ser Asp Asp Pro Glu Pro Ser Gly Pro His
        595                 600                 605

Leu Pro Arg Val Met Leu Pro Gly Val Leu Ala Gly Val Ser Ala Glu
    610                 615                 620

Glu Ser Trp Ala Gly Pro Gln Pro Leu Glu Thr Leu Asp Thr
625                 630                 635
```

```
<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgcggatccg cccataccag gtctcatg                                      28

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccggaattcc tgcacatcct tcaatcttgc                                    30

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgcggatcca gcaggtgcca ctatgcac                                      28

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccgctcgagg tcttggctgc tcagtgag                                      28

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cgcggatccc ctcaaagtcc catcctcg                                      28

<210> SEQ ID NO 14
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 14
ccggaattcg actagatctg tcttctcaac                                    30
```